United States Patent [19]

Ueno

[11] Patent Number: 5,739,161

[45] Date of Patent: Apr. 14, 1998

[54] AGENT FOR TREATING HEPTO.BILIARY DISEASES

[75] Inventor: Ryuji Ueno, Nishinomiya, Japan

[73] Assignee: R-Tech Ueno, Ltd., Osaka-Fu, Japan

[21] Appl. No.: 797,940

[22] Filed: Feb. 12, 1997

Related U.S. Application Data

[63] Continuation of Ser. No. 454,742, May 31, 1995, abandoned.

[30] Foreign Application Priority Data

Jun. 3, 1994 [JP] Japan .................... 6-122487

[51] Int. Cl.$^6$ .................. A61K 31/557; C07C 415/00
[52] U.S. Cl. .................. 514/530; 514/573; 560/121; 562/503
[58] Field of Search ............ 560/121; 562/503; 514/530, 573

[56] References Cited

U.S. PATENT DOCUMENTS

| | | | |
|---|---|---|---|
| 4,306,078 | 12/1981 | Holland et al. | 562/503 |
| 4,374,856 | 2/1983 | Ruwart | 424/317 |
| 5,096,927 | 3/1992 | Ueno et al. | 514/530 |
| 5,166,174 | 11/1992 | Ueno et al. | 514/530 |
| 5,284,858 | 2/1994 | Ueno et al. | 514/530 |

FOREIGN PATENT DOCUMENTS

| | | |
|---|---|---|
| 0284180 | 9/1988 | European Pat. Off. . |
| 0310305 | 4/1989 | European Pat. Off. . |
| 0410551 | 1/1991 | European Pat. Off. . |
| 0424156 | 4/1991 | European Pat. Off. . |
| 0232055 | 2/1990 | Japan . |
| 2-32055 | 2/1990 | Japan . |

*Primary Examiner*—Robert Gerstl
*Attorney, Agent, or Firm*—Sughrue, Mion, Zinn, Macpeak & Seas, PLLC

[57] ABSTRACT

The object of the present invention is to provide a pharmaceutical composition for treatment of hepato.biliary disease reduced in side effect such as diarrhea, which comprises 16,16-difluoro-15-keto-PGs having at least one methyl group or ethyl group on the carbon atom at the 17- or 18-position or adjacent to the terminal methyl group of ω-chain as an essential component.

28 Claims, No Drawings

AGENT FOR TREATING HEPTO.BILIARY DISEASES

This is a continuation of application Ser. No. 08/454,742 filed May 31, 1995 now abandoned.

BACKGROUND OF THE INVENTION

The present invention relates to prostaglandin E derivatives and use thereof, which have not been concretely published before. The present invention provides an agent for treating hepato.biliary diseases free from or very little side effect such as diarrhoea.

Prostaglandins (referred to as PGs hereinafter) are members of class of organic carboxylic acids, which are contained in tissues or organs of human or most other mammalian, and exhibit a wide range of physiological activity. PGs found in nature generally have a prostanoic acid skeleton.

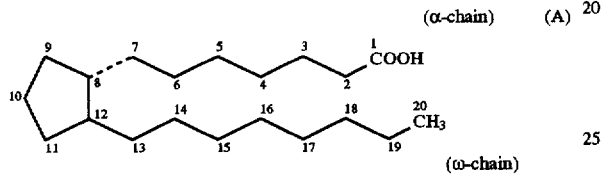

On the other hand, some of analogues have a modified skeleton. The primary PGs are classified to PGAs, PGBs, PGCs, PGDs, PGEs, PGFs, PGGs, PGHs, PGIs and PGJs according to the structure of the five-membered cycle moiety, and named hereafter by adding the subscript of 1, 2 or 3 at the right under position of the above A, B, . . . or J according to existence or non-existence of an unsaturated bond between 13–14 positions, 5–6 positions or 17–18 positions:

subscript 1: 13,14-unsaturated-15-OH
subscript 2: 5,6- and 13,14-diunsaturated-15-OH
subscript 3: 5,6-, 13,14-, and 17,18-triunsaturated-15-OH.

The PGFs are classified to, according to the configuration of the hydroxyl group at the 9-position, α type (the hydroxyl group is of an α-configuration) and β type (the hydroxyl group is of a β-configuration).

It was known that the primary $PGE_1$, $PGE_2$, and $PGE_3$ have a vasodilatation, hypotension, anemia achylia, intestinal hyeranakinezia, metratrophy, diuresis, bronchodilatation and anti-ulcer activity, and also primary $PGF_{1\alpha}$, $PGF_{2\alpha}$ and $PGF_{3\alpha}$ have a hypertension, vasoconstriction, intestinal hyeranakinezia, metratrophy, corpus luteum involution and bronchoconstriction.

U.S. Pat. No. 4,374,856 discloses that 15-methyl-$PGE_2$ and 16,16-dimethyl-$PGE_2$ have a hepatocyte protecting activity; Japanese Patent KOKAI Sho 58-164512 discloses that 15-cycloalkyl-6-oxo-$PGE_1$, 15-cycloalkyl-$PGI_1$ and $I_2$, 15-cycloalkyl-6,9α-nitrilo-$PGI_1$, and 15-cycloalkyl-6,9α-thio-$PGI_1$ and $I_2$ have a protecting activity for a cell including hepatocyte; Japanese Patent KOKAI Sho 58-203911 discloses that 6-oxo-$PGE_1$s and $PGI_1$s which have methyl groups at one or two positions of 15, 16, 17 and 20 or specific 15-cyclopentyl-$PGI_1$s have a cell protecting activity including hepatocyte; Japanese Patent KOKAI Sho 62-129218 discloses that 4- or 7-thia-$PGE_1$s can be used as an agent for treating hepatopathy. These, however, do not correspond to 15-keto-PGs or the derivatives.

EP-A1-0310305 (Japanese Patent KOKAI Hei 2-109) discloses that 15-keto-16-halo-PGs has an enteropooling activity and can be used as catharitics.

EP-A1-0424156 (Japanese Patent KOKAI Hei 3-204816, which is referred to as Publn. A hereinafter) discloses that 15-keto-PGs are effective to the treatment of hepato.biliary diseases, and said 15-keto-PGs include PGs substituted with fluorine atoms at the 16-position and having specific branches on the ω-chain in a general expression. But it includes no concrete disclosure (Example) of these compounds and does not suggest the difference from others in pharmacological properties.

EP-A1-0284180 (Japanese Patent KOKAI Sho 64-52753, which is referred to as Publn. B hereinafter) and Japanese Patent KOKAI Hei 2-32055 (referred to as Publn. C hereinafter) discloses that (13,14-dihydro-)15-keto-16,16-difluoro-PGE has an antiulcer activity, and said compound includes the compounds having specific branches on the ω-chain in concept. But, said compound is not concretely disclosed in the Examples, and the differences from the other compounds in the pharmacological activity are not disclosed.

SUMMARY OF THE INVENTION

The present invention provides of novel compound of 15-keto-16,16-difluoro-PGEs having an lower alkyl substituent in ω-chain which may be extended, and an agent for treating hepato.biliary diseases containing thereof.

The present invention relates to a compound represented by formula (I):

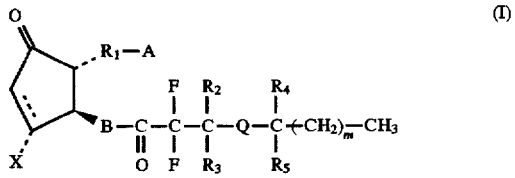

wherein A is —COOH, pharmaceutically acceptable salts thereof or esters which can be hydrolyzed by an esterase;

B is —$CH_2$— $CH_2$— or —CH═CH—,

X is a hydrogen atom or a hydroxyl group provided that X is a hydrogen atom when the five-membered cycle moiety has a double bond;

$R_1$ is a divalent saturated or unsaturated $C_6$ aliphatic hydrocarbon group;

$R_2$, $R_3$, $R_4$ and $R_5$ are independently a hydrogen atom, a methyl group or an ethyl group provided that at least one of them is a methyl group or an ethyl group;

Q is a saturated $C_1$–$C_6$ aliphatic hydrocarbon group which may have a branch; and m is 0 or 1, and an agent for treating hepato.biliary diseases consisting essentially of said compound.

Though the compounds represented by the above formula (I) are conceptionally included in the compounds described in the Publn. A, Publn. B and Publn. C as aforementioned, these have not been concretely disclosed in any literatures which have been published. The compounds of the formula (I) are excellent in the exhibition and duration of medical effect for hepato.biliary diseases without or little side effects in comparison with compounds concretely disclosed in the Publns. A, B and C.

The term "hepato.biliary diseases" in the present invention includes all conditions having etiology based on or accompanied by disorder of hepatocyte and conditions having etiology based on or accompanied by disorder of biliary truct, for example, hepatopathy; fulminant hepatitis, fatty liver (especially alcoholic fatty liver), hepatic coma, various acute or chronic hepatitis (alcoholic hepatitis, toxic hepatitis, A type viral hepatitis, B type viral hepatitis, non A/non B viral hepatitis, serum hepatitis, active chronic hepatitis etc.), hepatolenticular degeneration, hepatic hypertrophy, portal hypertension, obstructive jaundice, hepatic abscess, cirrhosis (especially alcoholic cirrhosis, biliary cirrhosis), parasitic hepatophyma, hepatic tuberculosis, cholecystisis, cholelithiasis, cholangitis, biliary colic, fat hypersensitivity and the like.

The term "treatment" in the present specification refers to any means of control of a disease in a mammal, including preventing the disease, curing the disease, relieving the disease and arresting or relieving the development of the disease.

In the present specification the numbering of the prostanoic acid indicated in formula (A) is used for the nomenclature of PGE derivatives. The formula (A) represents the basic skeleton of PGs having the carbon number of 20, and in the present specification the carbon of the carboxylic acid is numbered as 1; and 2 to 7 are numbered on the other carbons of the α-chain forward the five-membered ring; 8 to 12 are numbered on the carbon of the five-membered ring; and 13 and more are numbered on the ω-chain. In the compounds in which the carbon number exceeds 20 on the ω-chain the group containing the excess carbons is nominated as a substituent at the 20-position, and the compounds decreased in the number of carbon atoms on the ω-chain are nominated as decreasing the carbon number.

The configuration is nominated according with the basic skeleton as aforementioned unless otherwise specified.

The above formula represents the most typical configuration, a specific one, and the compounds of the present invention have this configuration unless otherwise specified.

As aforementioned the nomenclature of PGE derivatives are made according to the prostanoic acid skeleton, but they can be made according to the IUPAC. The concrete examples according to IUPAC are shown in Synthetic Examples.

PG derivatives used in the present invention may be saturated, unsaturated at the 13–14 position ($PG_1$ type), or unsaturated at the 13–14 position and the 5–6 position ($PG_2$ type). These derivertives may include 13,14-dihydro compounds.

The term "unsaturated" used in the definition of $R_1$ in the above formula means that the main or branched chain contains at least one of double bonds and/or triple bonds independently, separately or continuously. According to a usual nomenclature the position of an unsaturated bond is between adjacent two carbon atoms indicated by the younger number of the carbon atoms constituting the double bond, and the position of a discontinuous unsaturated bond is between separate two carbon atoms is shown by indicating the positions of both the carbon atoms. A preferable unsaturated bond is a double bond at the 2-position and a double bond or a triple bond at the 5-position.

The term "$C_6$-aliphatic hydrocarbons" means a hydrocarbon having a carbon number of 6 in a linear hydrocarbon chain (the carbon number is expressed by the same manner hereinafter), which may have one or more branches (the carbon number of the branch is preferably 1 to 3).

Concrete examples of $R_1$ are as follows:

$$-CH_2-CH_2-CH_2-CH_2-CH_2-CH_2-,$$

$$-CH_2-CH=CH-CH_2-CH_2-CH_2-,$$

-continued
$$-CH_2-CH_2-CH_2-CH_2-CH=CH-,$$

$$-CH_2-C\equiv C-CH_2-CH_2-CH_2-$$

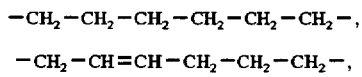

and the like.

As a suitable "pharmaceutically acceptable salt" a conventional non-toxic salt is included. The examples of such salt may be salts of inorganic base such as alkaline metal salts (sodium salts, potassium salts etc.), alkaline earth metal salts (calcium salts, magnesium salts etc.), ammonium salts; salts of organic base such as amines (for instance, methylamine salts, dimethylamine salts, cyclohexylamine salts, benzylamine salts, piperidine salts, ethylenediamine salts, ethanolamine salts, diethanolamine salts, triethanolamine salts, tris(hydroxymethylamino)ethane salts, monomethylmonoethanolamine salts, lysine salts, procaine salts, caffeine salts, etc.); basic amino acid salts (for example, arginine salts, lysine salts etc.), tetraalkyl ammonium salts and the like. These salts can be prepared from corresponding acids and bases according to a usual manner or a salt exchange manner.

"Esters hydrolyzable by esterases" are esters which can be hydrolyzed to the corresponding carboxylic acids and alcohols by the action of esterase, animal ester hydrolase, which is administered into a mammal including a human, corresponding carboxylic acids are produced.

Examples of these esters are aliphatic esters including lower alkyl esters such as methyl esters, ethyl esters, propyl esters, isopropyl esters, butyl esters, isobutyl esters, t-butyl esters, pentyl esters, 1-cyclopropyl ethyl esters and the like; lower alkenyl esters such as vinyl esters, allyl esters and the like; lower alkynyl esters such as ethynyl esters, propynyl esters; hydroxy (lower)alkyl esters such as hydroxy ethyl esters; lower alkoxy (lower)alkyl esters such as methoxy methyl esters, 1-methoxy ethyl esters and the like; and aryl (lower)alkyl esters including aryl esters which may be substituted, such as phenyl esters, tosyl esters, t-butylphenyl esters, salicyl esters, 3,4-dimethoxyphenyl esters, benzamide phenyl esters, and the like; aryl (lower)alkyl esters such as benzyl esters, trityl esters, benzhydryl esters and the like.

The configuration of the ring, α-, and/or ω-chain in FIG. (I) may be the same as the configuration of primary PGs or may be different. The present invention, however, may include mixture of compounds having a primary configuration and compounds having a unprimary configuration.

The compounds used in the present invention may cause keto-hemiacetal balance due to the formation of hemiacetal between the hydroxyl group at the 1 1-position and the keto-group at the 15-position when the bond between the 13 and 14 positions is saturated. When such tautomers exist, the ratio of each tautomer varies according to the structure of the other portion and kind of substituents, though there is a case that one of the tautomers exists remarkably more than the other, the compounds of the present invention include the both tautomers. In the present specification the compounds are often represented by the formula or nomenclature of keto type regardless of the presence of such tautomers, but it is only for the sake of convenience, and is not intended to exclude hemiacetal compounds.

According to the present invention an individual tautomer, a mixture thereof, an optical isomer, a mixture thereof, a racemic compound, other stereoisomer and the like can be used for the same purpose.

The above PGE derivertives have activity for prevention or treatment of disorder of hepatocytes or biliary cells, so they are useful for the treatment of hepato.biliary diseases. Such activity can be determined using a standard process such as galactosamine disorder model.

The compounds usable in the present invention can be used as a medicine for animals or a human, and can be administered systemically or topically or orally, by intravenous injection including drip, subcutaneous injection, intrarectal administration and the like. The dose depends on the sort of animals or a human to be administered to, age, weight, conditions thereof, desired medical effect, method of administration, term of treatment and so on, but a sufficient effect can be achieved by 1 to 1000 μg/kg(p.o.) dose, when the compounds are administered 2 or 4 times a day or continuously.

A solid composition for oral administration in the present invention includes a tablet, a troche, a sublingual tablet, a capsule, a pill, a powder, a granular and the like. In such a solid composition one or more active substances are mixed with at least one of inactive diluents such as lactose, mannitol, glucose, hydroxypropyl cellulose, microcrystalline cellulose, starch, polyvinyl pyrrolidone, magnesium metasilicic aluminate and the like. According to a conventional manner the composition of the present invention may contain additives other than the above inert diluents, for example, a lubricant such as magnesium stearate, a disintegrator calcium cellulose gluconate, a stabilizer such as an etherified cyclodextrin, e.g. α, β- or γ-cyclodextrin, dimethyl-α-, dimethyl-β-, trimethyl-β- or hydroxypropyl-β- cyclodextrin and the like; a branched cyclodextrin, e.g. glycosyl-, maltosyl-cyclodextrin and the like, formylated cyclodextrin, a sulfur-containing cyclodextrin, misoprostol, a phospholipid and the like. When the above cyclodextrin is used, the compounds of the present invention often form clathrates with the cyclodextrin to increase the stability. When phospholipids are used, the compounds of the present invention form sometimes liposomes so as to be increased in the stability. Tablets or pills may be coated with a film soluble in the stomach or in the bowels, for example, white sugar, gelatin, hydroxypropyl cellulose, hydroxypropyl methyl cellulose phthalate and the like, or coated with two or more layers. Further, the compounds may be encapsulated with a material to be disintegrated such as gelatin. When a prompt effect is required, the compounds are provided as a sublingual tablet. Glycerin, lactose and the like may be used as a substrate.

As a liquid composition for oral administration an emulsion, a liquor, a suspension, a syrup, an elixir and the like may be exemplified. A general inert diluent, for example, purified water, ethanol and the like may be contained. This composition may contain a wetting agent, an adjuvant such as a suspending agent, an edulcorant, a flavor, an aromatic, a preservative and the like.

Other form of the composition for the oral administration may include a spray which contains one or more active ingredients, and formulated by a usual manner.

A composition for injection includes a solution in sterilized water or an organic solvent, a suspension, and an emulsion. As a medium for an aqueous solution or a suspension distilled water for injection, a physiological salt solution and a Ringer's solution are, exemplified.

As the organic solvent or a medium for suspension propylene glycol, polyethylene glycol, a vegetable oil such as olive oil, alcohol such as ethanol, polysolvate and the like are exemplified. Such a composition may additionally contain an adjuvant such as preservatives, wetting agents, emulsifiers, and suspending agents. These materials are sterilized by filtration through a filter retaining bacteria, a bactericide, gas-sterilization, radio sterilization and the like. These compounds may be previously prepared as sterilized solid composition, which may be dissolved in to sterilized water or a sterilized solvent for injection just before use.

Another type of the composition is a suppository or a pessary. The suppository or pessary can be prepared mixing an active compound with a substrate which is softened at body temperature, for example, cacao butter, and the absorbability may be improved by a nonionic surface active agent having a suitable softening temperature.

The present invention also provides a method for treatment of hepato.biliary diseases by administration of the composition of the present invention to a patient.

The present invention is concretely illustrated according to the Examples (Synthetic Examples and Testing Example). In the Examples following abbreviations are used for the corresponding compounds.

THF: tetrahydrofuran,

DMSO: dimethylsulfoxide,

DBU: 1,8-azabicyclo[5.4.0]undeca-7-en

EXPERIMENTS

EXAMPLE 1

1: Preparation of Z-7-[(1R,2R,3R)-2-(4,4-difluoro-7-methyl-3-oxooctyl)-3-hydroxy-5-oxocyclopentyl] hept-5-enoic acid(13,14-dihydro-15-keto-16,16-difluoro-19-methyl-PGE₂) (12)

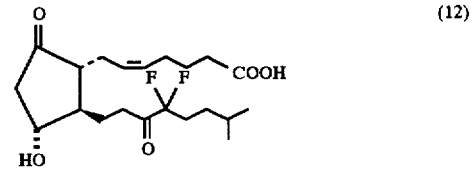

(12)

1-1: (1S,5R,6R,7R)-6-(E-4,4-difluoro-7-methyl-3-oxooct-1-enyl)-7-(tetrahydropyranyloxy)-2-oxabicyclo[3.3.0]octan-3-one (4)

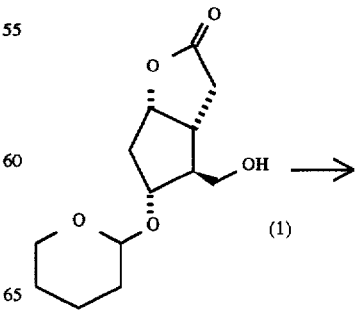

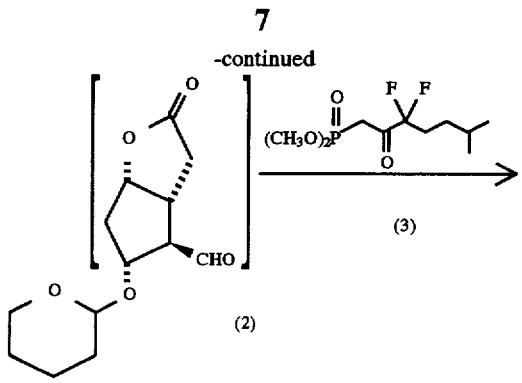

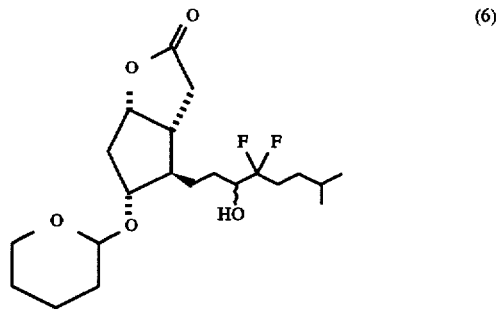

A solution of Corey lactone, (1S,5R,6R,7R)-6-(hydroxymethyl)-7-(tetrahydropyranyioxy)-2-oxabicyclo[3.3.0]octan-3-one (1), (6.800 g) in dichloromethane (40 ml) was oxidized by means of Swern oxidetion with using a solution of oxalyl chloride (2M dichloromethan solution, 30 ml) in dichloromethane (100 ml), DMSO (8.45 ml), and triethylamine (16.9 ml). After the usual work up, Corey aldehyde, (1S,5R,6R,7R)-6-formyl-7-(tetrahydropyranyloxy)-2-oxabicyclo [3.3.0]octan-3-one (2) was obtained.

To the suspension of sodium hydride (60%, 1.273 g) in THF (50 ml) was added a solution of dimethyl (3,3-difluoro-6-methyl-2-oxoheptyl)phosphonate (3) (8.664 g) in THF (10 ml). After stirring for 1 hr, zinc chloride (4.337 g) was added, and the resultant was stirred for additional 1 hour, A solution of Corey aldehyde (2) in THF (20 ml) was added, followed by stirring for 15 hours at room temperature. The crude material obtained after the usual work up was chromatographed on silica gel eluted with a mixed soluent of n-hexane and ethyl acetate (3/1) to yield the compound (4).

Yield: 6.144 g (57.8%)

1-2: (1S,5R,6R,7R)-6-(4,4-difluoro-7-methyl-3-oxooctyl)-7-(tetrahydropyranyloxy)-2-oxabicyclo[3.3.0]octan-3-one (5)

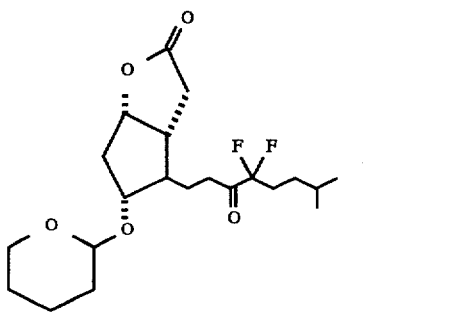

A solution of the compound (4) (6.144 g) in THF (40 ml) was added by dimethylphenylsilane (3.17 ml) and Wilkinson's catalist (0.142 g), followed by stirring for 2 hours at 50° C. The crude material obtained after the usual work up was chromatographed on silica gel eluted with a mixed soluent of n-hexane and ethyl acetate (2/1–3/2) to yield the compound (5).

Yield: 3.386 g (54.8%)

1-3: (1S,5R,6R,7R)-6-{4,4-difluoro-3(RS)-hydroxy-7-methyloctyl}-7-(tetrahydropyranyloxy)-2-oxabicyclo[3.3.0]octan-3-one (6)

Sodium borohydride (0.138 g) was added to the solution of the compound (5) (3.386 g) in methanol (50 ml), followed by stirring at 0° C. for 10 minutes. The crude product obtained after the usual work up was chromatographed on silica gel eluted with a mixed solvent of n-hexane and ethyl acetate (1/1) to give the compound (6).

Yield: 3.183 g (93.5%)

1-4: Z-7-[(1R,2R,3R,5S)-2-{4,4-difluoro-3(RS)-hydroxy-7-methyloctyl}5-hydroxy-3-(tetrahydropyranyloxy)cyclopentyl]hept-5-enoic acid (8)

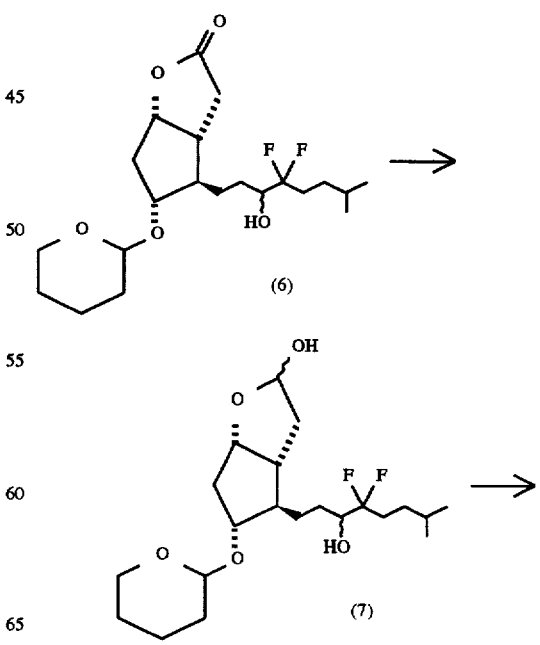

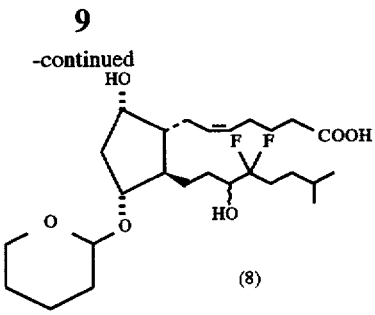

A solution of the compound (6) (2.883 g) in toluene (70 ml) was cooled at −78° C., followed by addition of diisobutylaluminumhydride (1M toluene solution, 17.8 ml), the resultant was stirred for 1 hour. After the usual work up, the lactol (7), {1S,3(RS),6R,7R}-6-{4,4-difluoro-3(RS)-hydroxy-7-methyloctyl}-7-(tetrahydropranloxy)-2-oxabicyclo[3.3.0]octan-3-ol (7), was obtained.

A suspension of (4-carboxybutyl)triphenylphosphonium bromide (12.64 g) in THF (50 ml) was treated with potasium t-butoxide (1M THF solution, 57.0 ml) to generate the corresponding ylide. A solution of the lactol (7) in THF (30 ml) was added to the generated ylide cooled at −30° C., followed by stirring for 15 hours. After the usual work up, the carboxylic acid, Z-7-[(1R,2R,3R,5S)-2-{4,4-difluoro-3(RS)-hydroxy-7-methyloctyl}-5-hydroxy-3-(tetrahydropyranyloxy)cyclopentyl]hept-5-enoic acid (8), was obtained.

1-5: Phenacyl Z-7-[(1R,2R,3R,5S)-2-{4,4-difluoro-3(RS)-hydroxy-7-methyloctyl}-5-hydroxy-3-(tetrahydropyranyloxy)cyclopentyl]hept-5-enoate (9)

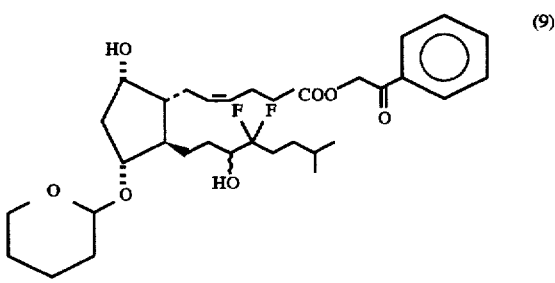

Diisopropylethylamine (4.73 ml) and phenacyl bromide (5.67 g) were added to a solution of the carboxylic acid (8) in acetonitrile (50 ml), and the resultant was heated at 45° C. for 2 hours. The crude material obtained after the usual work up was chromatographed on silica gel eluted with a mixed solvent of n-hexane and ethyl acetate (3/2) to give the compound (9).

Yield: 3.618 g (83.4% for the three reaction steps)

1-6: Phenacyl Z-7-[(1R,2R,3R)-2-(4,4-difluoro-7-methyl-3-oxootyl)-3-(tetrahydropyranyloxy)-5-oxocyclopentyl]hept-5-enoate (10)

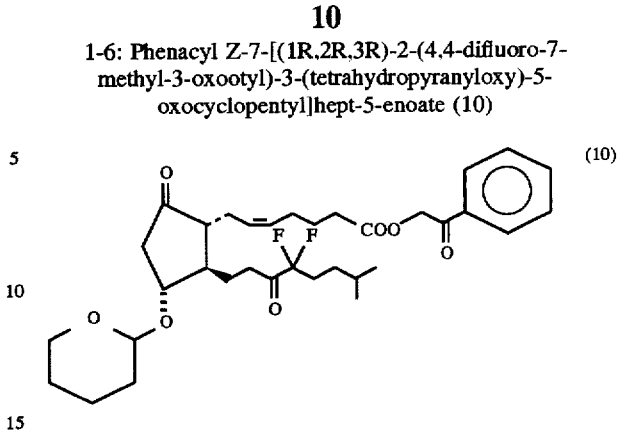

The compound (9) was oxidized by means of Swern oxidation with using a diluted solution of oxalyl chloride (2M dichloromethan solution, 17.8 ml) in dichloromethane (50 ml), DMSO (5.1 ml), and triethylamine (10 ml). The crude product obtained after the usual work up was chromatographed on silica gel eluted with a mixed solvent of n-hexane and ethyl acetate (2/1) to give the compound (10).

Yield: 3.034 g (84.4%)

1-7: Phenacyl Z-7-[(1R,2R,3R)-2-(4,4-difluoro-7-methyl-3-oxooctyl)-3-hydroxy-5-oxocyclopentyl]hept-5-enoate (11)

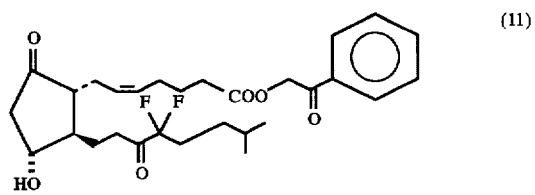

A solution of the compound (10) (3.034 g) in a mixed solvent of acetic acid, THF, and water (3/1/1) was maintained at 50° C. for 3 hours. The crude product obtained after the usual work up was chromatographed on silica gel eluted with a mixed solvent of n-hexane and ethyl acetate (3/1) to give the compound (11).

Yield: 1.945 g (74.4%)

1-8: Z-7-[(1R,2R,3R)-2-(4,4-difluoro-7-methyl-3-oxooctyl)-3-hydroxy-5-oxocyclopentyl]hept-5-enoic acid (12)

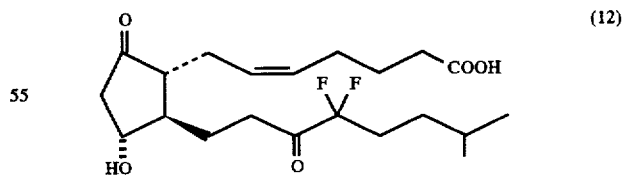

A solution of the compound (11) (0.362 g) in acetic acid was treated with zinc (0.724 g) for several hours with stirring. The crude product obtained after the usual work up was chromatographed on silica gel eluted with a mixed solvent of dichloromethane and methanol (25/1) to give the compound (12).

Yield: 0.235 g (84%)

n. m. r. (CDCl₃) δ: 0.92 (6H, d, J=6.0 Hz), 1.33–2.74 (19H, m), 2.36 (2H, t, J=7.0 Hz), 4.19 (1H, m), 5.40 (2H, m).

mass m/z :402 (M⁺), 384 (M⁺−H₂O), 366 (M⁺−2H₂O),

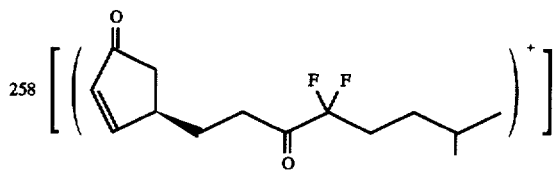

EXAMPLE 2

2: Preparation of 7-[(1R,2R,3R)-2-(4,4-difluoro-7-methyl-3-oxooctyl)-3-hydroxy-5-oxocyclopentyl]heptanoic acid (2-16) (13,14-dihydro-15-keto-16,16-difluoro-19-methyl-PGE₁)

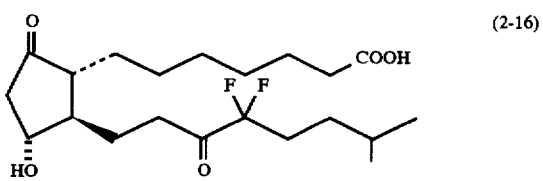

2-1: {1S,5R,3(RS),6R,7R}-6-(t-butyldimethylsiloxymethyl)-7-(tetrahydropyranyloxy)-2-oxabicyclo[3.3.0]octan-3-ol (2-2)

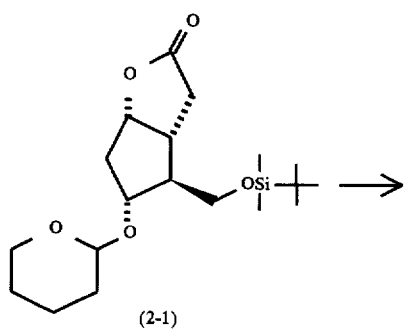

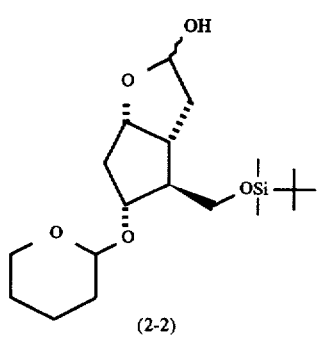

A solution of Corey lactone, (1S,5R,6R,7R)-6-(t-butyldimethylsiloxymethyl)-7-(tetra-hydropyranyloxy)-2-oxabicyclo[3.3.0]octan-3-one (1) (15.0 g) in toluene (75 ml) was treated with diisopropylaluminumhydride (1M toluene solution, 61 ml) at −78° C. The usual work up yielded the lactol (2-2).

Yield: 15.32 g (104%)

2-2: Z-7-[(1R,2R,3R,5S)-2-(t-butyldimethylsyloxymethyl)-5-hydroxy-3-(tetrahydropyranyloxy)cyclopentyl]hept-5-enoic acid (2-3)

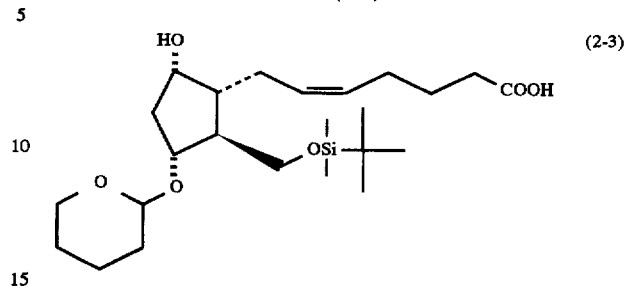

A suspension of (4-carboxybutyl)triphenylphosphonium bromide in THF (110 ml) was treated with potasium t-butoxide (1M THF solution, 247 ml) at 0° C. to generate the corresponding ylide. A solution of the lactol (2-2) in THF (50 ml) was added to the generated ylide, followed by stirring for 1.5 hours at room temperature. The usual work up yielded the carboxylic acid (2-3).

Yield: 36.62 g 2-3: Isopropyl Z-7-[(1R,2R,3R,5S)-2-(t-butyldimethylsiloxymethyl)-5-hydroxy-3-(tetrahydropyranyloxy)cyclopentyl]hept-5-enoate (2-4)

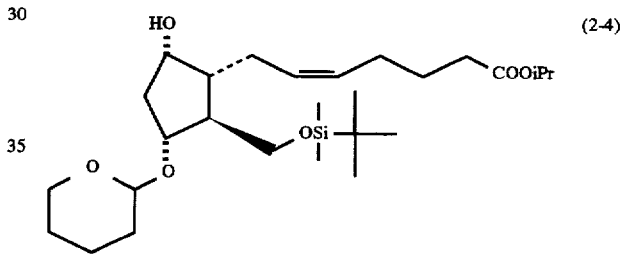

A solution of carboxylic acid (2-3) in acetonitrile (150 ml) was treated with isopropyl iodide (24.0 ml) and DBU (36.0 ml) at room temperature to yield the corresponding isopropyl ester (2-4). The crude product obtained after the usual work up was chromatographed on silica gel eluted with a mixed solvent of n-hexane and ethyl acetate (5/1–3/1) to yield the compound (2-4).

Yield: 18.32 g (90.7% for the three reaction steps)

2-4: Isopropyl Z-7-[(1R,2R,3R,5S)-5-acetoxy-2-(t-butyldimethylsiloxymethyl)-3-(tetrahydropyranyloxy)cyclopentyl]hept-5-enoate (2-5)

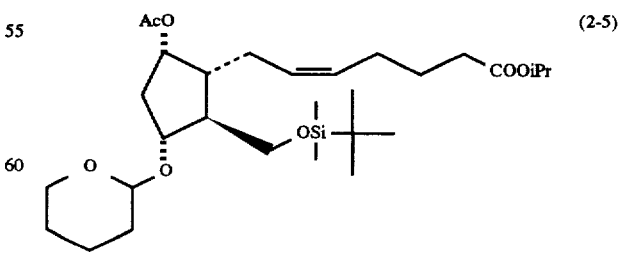

Pyridine (8.9 ml) and acetylchloride (7.8 ml) were added to a solution of the compound (2-4) (18.32 g) in dichloromenthane (90ml) at 0° C., followed by stirring for 30 minites and 1.5 hours at room temperature. After the usual work up, the compound (2-5) was obtained.

Yeild: 20.09 g

2:5: Isopropyl Z-7-[(1R,2R,3R,5S)-5-acetoxy-2-(hydroxymethyl)-3-(tetrahydropyranyloxy)cyclopentyl]hept-5-enoate (2-6)

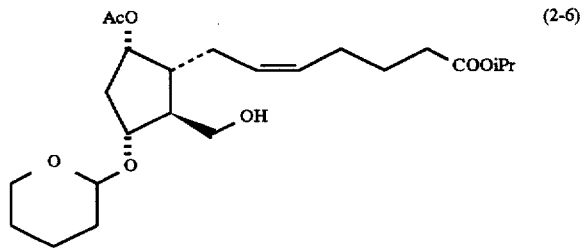

To a solution of the compound (2-5) (20.09 g) in THF (50 ml) was added tetrabutylamonium fluoride (1M THF solution, 74.3 ml), followed by stirring overnight at room temperature. The crude product obtained after the usual work up was chromatographed on silica gel eluted with a mixed solvent of n-hexane and ethyl acetate (2/3) to give the compound (2-6).

Yield: 15.50 g (98.9% for the two reaction steps)

2-6: Isopropyl 7-[(1R,2R,3R,5S)-5-acetoxy-2-(hydroxymethyl)-3-(tetrahydropyranyloxy)cyclopentyl]heptanoate (2-7)

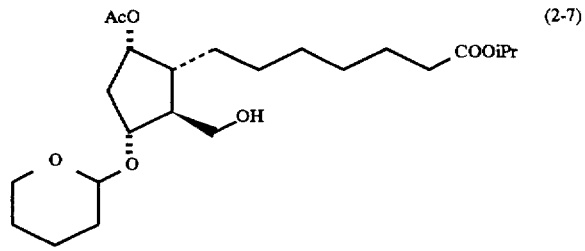

The compound (2-6) (15.50 g) in ethyl acetate (20 ml) was reduced with 5% Pd on carbon under hydrogen atmosphere.

Yield: 15.50 g 2-7: Isopropyl 7-[(1R,2R,3R,5S)-5-acetoxy-2-formyl-3-(tetrahydropyranyloxy)cyclopentyl]heptanoate (2-8)

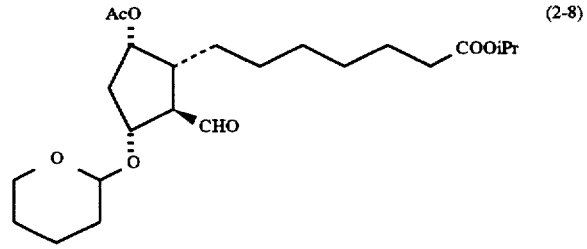

The compound (2-7) (15.50 g) in dichloromethane (100 ml) was oxidized by means of Swern oxidation using oxalyl chloride (2M dichloromethane solution, 54.3 ml), DMSO (15.4 ml), and triethylamine (50.0 ml). The crude product obtained after the usual work up was chromatographed on silica gel eluted with a mixed soluent of n-hexane and ethyl acetate (7/3) to yield the compound (2-8).

Yield: 15.21 g (98.1%)

2-8: Isopropyl 7-[(1R,2R,3R,5S)-5-acetoxy-2-(E-4,4-difluoro-7-methyl-3-oxooct-1-enyl)-3-(tetrahydropyranyloxy)cyclopentyl]heptanoate (2-10)

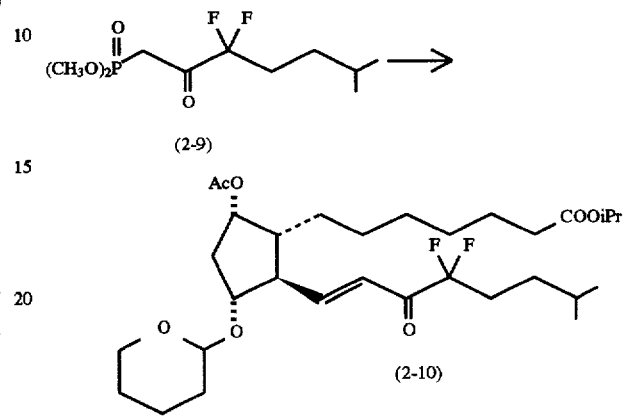

To a solution of potasium t-butoxide (2M THF solution, 14.9 ml) was added a solution of dimethyl(3,3-difluoro-6-methyl-2-oxoheptyl)phosphonate (2-9) (4.079 g) in THF (20.4 ml), followed by stirring for 30 minutes at room temperature. To the solution was added zinc chloride (2.027 g), followed by stirring for 30 minutes at room temperature. After addition of the aldehyde (2-8) (2.883 g) in THF (14 ml), the reaction mixture was heated under reflux for 62 hours. The crude material obtained after the usual work up was chromatographed on silica gel eluted with a mixed solvent of n-hexane and ethyl acetate (4/1) to give the compound (2-10).

Yield: 3.393 g (87.5%)

2-11: Benzyl 7-[(1R,2R,3R,5S)-2-(4,4-difluoro-7-methyl-3-oxooctyl)-5-hydroxy-3-(tetrahydropyranyloxy)cyclopentyl]heptanoate (2-13)

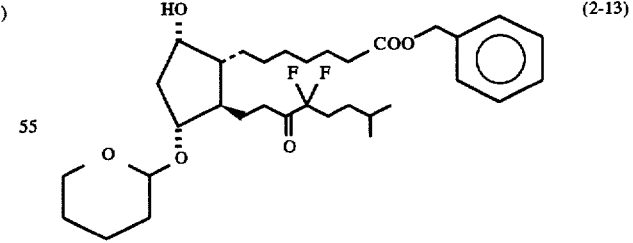

The compound (2-12) (1.828 g) in acetonitrile (18 ml) was treated with DBU (1.04 ml) and benzyliodide (0.83 ml) for 2.5 hours at room temperature.

Yield: 1.717 g (84.7% for the two reaction steps)

2-12: Benzyl 7-[(1R,2R,3R,5S)-2-(4,4-difluoro-7-methyl-3-oxooctyl)-3-(tetrahydropyranyloxy)-5-oxocyclopentyl]heptanoate (2-14)

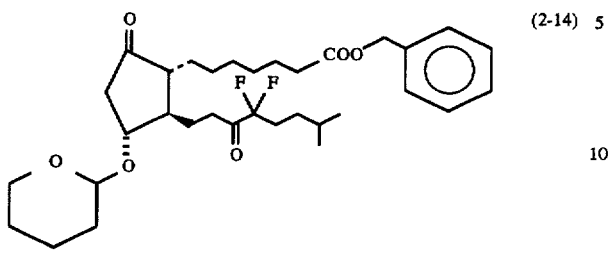
(2-14)

The compound (2-13) (1.700 g) in dichloromethane (17 ml) was oxidized by means of Swern oxidation using a solution of oxalylchloride (0.51 ml) in dichloromethane (5.1 ml), DMSO (0.83 ml), and triethylamine (3.27 ml). The crude product obtained after the usual work up was chromatographed on silica gel eluted with a mixed solvent of n-hexane and ethyl acetate (3/1) to yield the compound (2-14).

Yield: 1.574 g (92.8%)

2-13: Benzyl 7-[(1R,2R,3R)-2-(4,4-difluoro-7-methyl-3-oxoocty)-3-hydroxy-5-oxocyclopentyl]heptanoate (2-15)

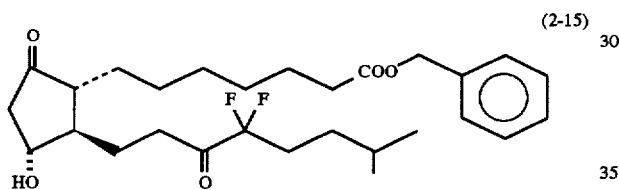
(2-15)

A solution of the compound (2-14) (1.565 g) in a mixed solvent (70 ml) of acetic acid, water, and THF (4/2/1) was maintained at 45° C. for 3 hours with stirring. The crude product obtained after the usual work up was chromatographed on silica gel eluted with a mixed soluent of n-hexane and ethyl acetate (4/1) to yield the compound (2-15).

Yield: 1.169 g (87%)

2-14: 7-[(1R,2R,3R)-2-(4,4-difluoro-7-methyl-3-oxooctyl)-3-hydroxy-5-oxocyclopentyl]heptanoic acid (2-16)

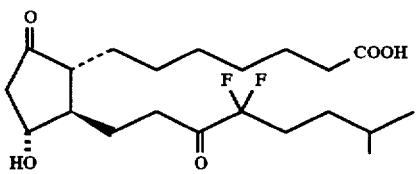
(2-16)

The compound (2-15) (1.150 g) in ethanol (20 ml) was hydrogenated with 5% Pd on carbon (0.230 g) under hydrogen atmosphere. The crude product obtained after the usual work up was chromatographed on silica gel eluted with a mixed soluent of n-hexane and ethyl acetate (100/0-40/60) to yield the compound (2-16).

Yield: 0.731 g (78%)

n. m. r. (CDCl$_3$) δ: 0.92 (6H, d, J=6.0 Hz), 1.20–2.13 (22H, m), 2.26 (1H, dd, J=17.5 Hz, J=11.5 Hz), 2.60 (1H, dd, J=17.5 Hz, J=7.0 Hz), 4.19 (1H, m).

mass m/z: 404 (M$^+$), 386 (M$^+$–H$_2$O), 368 (M$^+$–2H$_2$O),

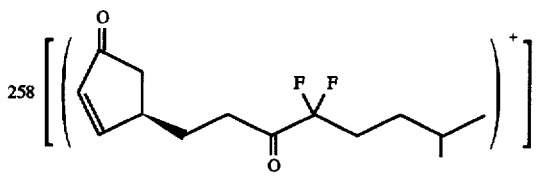

EXAMPLE 3

3: Preparation of 7-[(1R,2R,3R)-2-{4,4-difluoro-5(R)-methyl-3-oxooctyl}-3-hydroxy-5-oxocyclopentyl]heptanoic acid (3-10) (13,14-dihydro-15-keto-16,16-difluoro-17(R)-methyl-PGE$_1$)

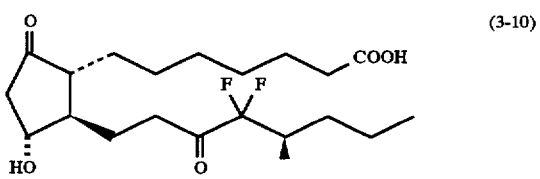
(3-10)

3-1: Methyl 7-[(1R,2R,3R,5S)-5-acetoxy-2-{E-4,4-difluoro-5(R)-methyl-3-oxooct-1-enyl}-3-(tetrahydropyranyloxy)cyclopentyl]heptanoate (3-3)

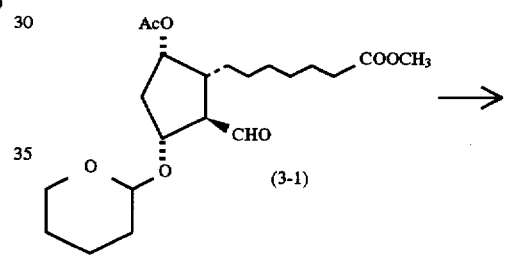

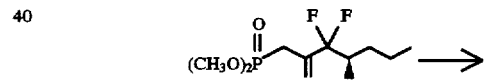

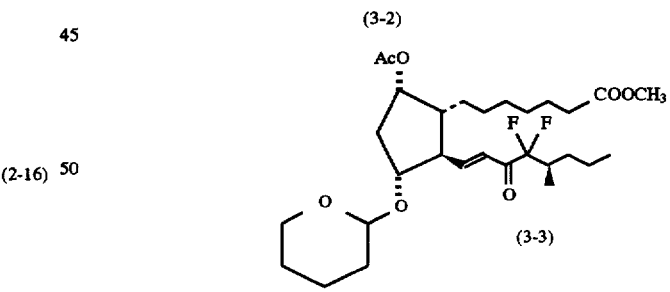

The two isomers of the amide obtained from (dl)-2,2-difluoro- 3-methylhexanoic acid and (R)-(+)-phenylethylamine were separated from each other by means of normal phase chromatography. Dimethyl{3,3-difluoro-4(R)-methylheptyl}phosphonate (3-2) (0.796 g) prepared from the amide having the shorter retention time was treated in THF (5 ml) with potassium t-butoxide (1M THF solution, 2.63 ml) at room temperature with 30 minute stirring, followed by additon of zinc chloride (0.340 g). The resultant was stirred for 1 hour. To the resultant was added the aldehyde, prepared as described in Example 2 except for methyl iodide employed to replace isopropyliodide, methyl 7-[(1R,2R,3R,5S)-5-acetoxy-2-formyl-3-(tetrahydropyranyloxy)cyclopentyl]heptanoate (3-1) (0.825g) in THF (5ml), followed by heating under refluxing for 3 days. The crude product obtained after the usual work up was chromatographed on silica gel eluted with a mixed solvent of n-hexane and ethyl acetate (3/1) to yield the compound (3-3).

Yield: 0.664 g (59%)

3-2: Methyl 7-[(1R,2R,3R,5S)-5-acetoxy-2-{4,4-difluolro-5(R)-methyl-3-oxooctyl}-3-(tetrahydropyranyloxy)cyclopentyl]heptanoate (3-4)

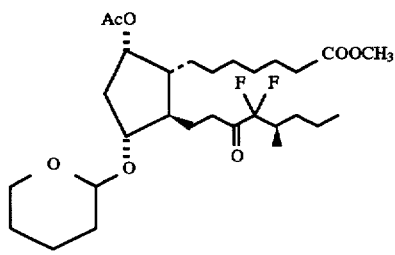
(3-4)

The compound (3-3) (0.632 g) in ethyl acetate (10 ml) was hydrogenated with 5% Pd on carbon (0.065 g) under hydrogen atmosphere to yield the compound (3-4).

Yield: 0.631 g (100%)

3-3: Methyl 7-[(1R,2R,3R,5S)-5-acetoxy-2-{4,4-difluoro-3(RS)-hydroxy-5(R)-methyloctyl}-3-(tetrahydropyranyloxy)cyclopentyl]heptanoate (3-5).

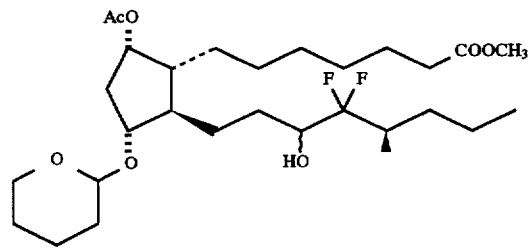
(3-5)

The compound (3-4) (0.630 g) in methanol (10 ml) at −40° C. was reduced with sodium borohydride (0.044 g). The crude product obtained after the usual work up was chromatographed on silica gel eluted with a mixed solvent of n-hexane and ethyl acetate (2/1) to yield the compound (3-5).

Yield: 0.619 g (98%)

3-4:7-[(1R,2R,3R,5S)-2-{4,4-difluoro-3(RS)-hydroxy-5(R)-methyloctyl}-5-hydoxy-3-(tetrahydropyranyloxy)cyclopentyl]heptanoic acid (3-6)

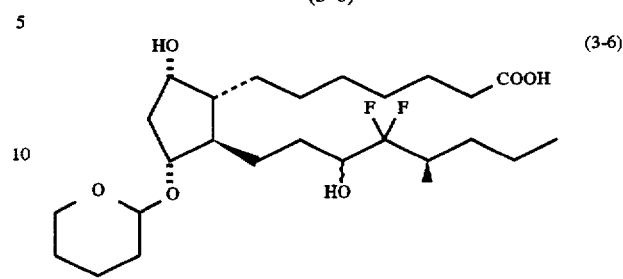
(3-6)

The compound (3-5) (0.619 g) in ethanol (11 ml) was treated with 1-N aqueous sodium hydroxide solution (11.3 ml) at room temperature with stirring to yield the compound (3-6).

Yield: 0.583 g 3-5: Benzyl 7-[(1R,2R,3R,5S)-2-{4,4-difluoro-3(RS)-hydroxy-5(R)-methyloctyl}-5-hydroxy-3-(tetrahydropyranyloxy)cyclopentyl]heptanoate (3-7)

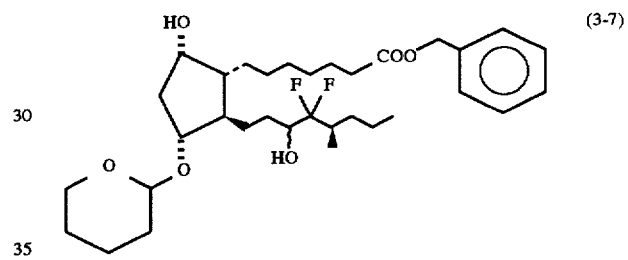
(3-7)

The compound (3-6) (0.583 g) was converted to the corresponding benzyl estel (3-7) with using diisopropylethylamine (0.79 ml) and benzyl bromide (0.54 ml). The desired compound was chromatographed on silica gel eluted with a mixed soluent of n-hexane and ethyl acetate (3/2).

Yield: 0.633 g (96% for the two reaction steps)

3-6: Benzyl 7-[(1R,2R,3R)-2-{4,4-difluoro-5(R)-methyl-3-oxooctyl}-3-(tetrahydropyranyloxy)-5-oxocyclopentyl]heptanoate (3-8)

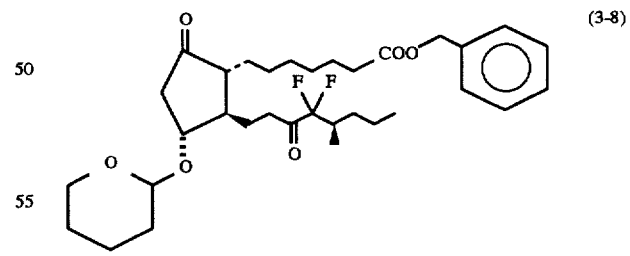
(3-8)

The compound (3-7) (0.633 g) in dichloromethane (7 ml) was oxidized by means of Swern oxidation with using a solution of oxalyl chloride (0.47 ml) in dichloromethane (10 ml), DMSO (0.77 ml), and triethylamine (1.89 ml), the crude product obtained after the usual work up was chromatographed on silica gel eluted with a mixed solvent of n-hexane and ethyl acetate (4/1) to yield the compound (3-8).

Yield: 0.593 g (94%)

3-7: Benzyl 7-[(1R,2R,3R)-2-{4,4-difluoro-5(R)-methyl-3-oxooctyl}- 3-hydroxy-5-oxocyclopentyl] heptanoate (3-9)

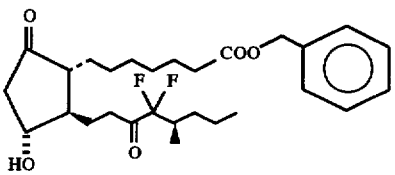
(3-9)

The compound (3-8) (0.590 g) was dissolued into THF (5 ml), followed by addition of acetic acid (20 ml) and water (10 ml). The resultant was maintained at 45° C. for 3.5 hours. The crude product obtained after the usual work up was chromatographed on silica gel eluted with a mixed soluent of n-hexane and ethyl acetate (7/3) to yield the compound (3-9).

Yield: 0.407 g (81%)

3-8: 7-[(1R,2R,3R)-2-{4,4-difluoro-5(R)-methyl-3-oxooctyl}-3-hydroxy-5-oxocyclopentyl]heptanoic acid (3-10)

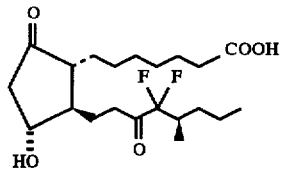
(3-10)

The compound (3-8) (0.407 g) in ethanol (15 ml) was hydrogenated with 10% Pd on carbon under hydrogen atmosphere. The crude product was chromatographed on silica gel eluted with a mixed soluent of n-hexane and ethyl acetate (100/0-30/70) to yield the compound (3-10).

Yield: 0.153 g (46%)

n. m. r. (CDCl$_3$) δ: 0.91 (3H, t, J=7.0 Hz), 1.00 (0.6H, d, J=7.0 Hz), 1.10 (0.4H, d, J=7.0 Hz), 1.13–2.30 (21H, m), 2.34 (2H, t, J=7.5 Hz), 2.58 (1H, dd, J=17.5 Hz, J=7.5 Hz), 2.62 (1H, dd, J=17.5 Hz, J=7.5 Hz), 2.90 (1H, t, J=7.5 Hz), 4.02–4.28 (1H, m)

mass m/z: 404 (M$^+$), 386 (M$^+$–H$_2$O), 368 (M$^+$–2H$_2$O),

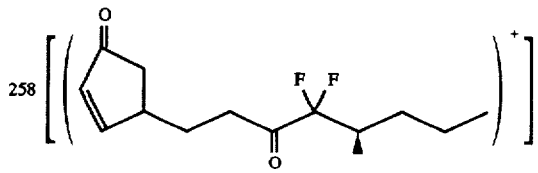

EXAMPLE 4

4: Preparation of 7-[(1R,2R,3R)-2-{(4,4-difluoro-5(S)-methyl-3-oxooctyl}-3-hydroxy-5-oxocyclopentyl]heptanoic acid (4-1) (13,14-dihydro-15-keto-16,16-difluoro-17(S)-methyl-PGE$_1$)

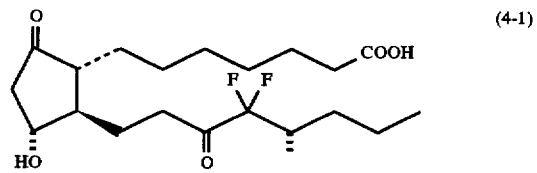
(4-1)

4-1: The compound (4-1) was prepared as described in Example 3 except for using dimethyl{3,3-difluoro-4(S)-methylheptyl}phosphonate (4-2) prepared from the amide isomer having the longer retention time when the two isomers of the amide generated from (dl)-2,2-difluoro-3-methylhexanoic acid and (R)-(+)-phenylethylamine were separated by means of normal phase chromatography.

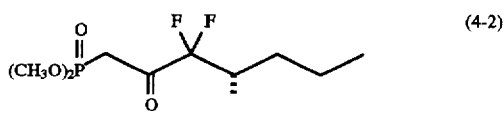
(4-2)

n. m. r. (CDCl$_3$) δ: 0.90 (3H, t, J=7.0 Hz), 0.98 (0.6H, d, J=7.0 Hz), 1.09 (0.4H, d, J=7.0 Hz), 1.14–2.30 (21H, m), 2.34 (2H, t, J=7.5 Hz), 2.67 (1H, dd, J=17.5 Hz, J=7.5 Hz), 2.70 (1H, dd, J=17.5 Hz, J=7.5 Hz), 2.90 (1H, t, J=7.5 Hz), 4.04–4.26 (1H,m).

mass m/z: 404 (M$^+$), 386 (M$^+$–H$_2$O), 368 (M$^+$–2H$_2$O),

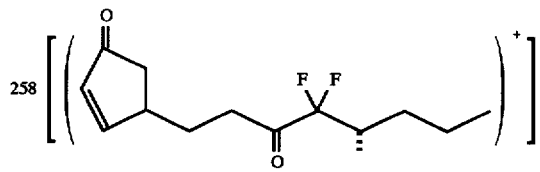

EXAMPLE 5

5: Preparation of 7-[(1R,2R,3R)-2-{4,4-difluoro-5(R),7-dimethyl-3-oxooctyl}-3-hydroxy-5-oxocyclopentyl]heptanoic acid (5-1) (13,14-dihydro-15-keto-16,16-difluoro-17(R),19-dimethyl-PGE$_1$)

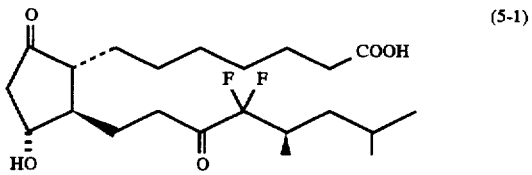
(5-1)

5-1: The compound (5-1) was prepared as described in Example 3 except for using dimethyl{3,3-difluoro-4(R),6-dimethyl-2-oxoheptyl}phosphonate (5-2) prepared from the amide isomer having the shorter retention time when the two isomers of the amide prepared from (dl)-2,2-difluoro-3,5- dimethylhexanoic acid and (R)-(+)-phenylethylamine were separated by means of normal phase chromatography.

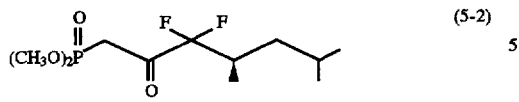
(5-2)

n. m. r. (CDCl₃) δ: 0.86 (4H, d, J=7.0 Hz), 0.94 (2H, d, J=7.0 Hz), 0.98 (0.7H, d, J=7.0 Hz), 1.08 (0.3H, d, J=7.0 Hz), 1.13-2.43 (20H, m), 2.34 (2H, t, J=6.5 Hz), 2.58 (1H, dd, J=17.5 Hz, J=7.5 Hz), 2.71 (1H, dd, J=17.5 Hz, J=7.5 Hz), 3.91 (1H, t, J=7.5 Hz), 4.03-4.30 (1H, m).

mass m/z: 418 (M⁺), 400 (M⁺–H₂O), 382 (M⁺–2H₂O),

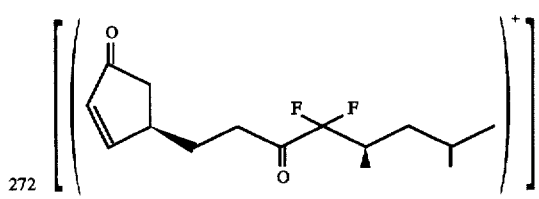
272

EXAMPLE 6

6: Preparation of 7-[(1R,2R)-2-(4,4-difluoro-7-methyl-3-oxooctyl)-5-oxocyclopentyl]heptanoic acid (6-3) (13,14-dihydro-15-keto-11-dehydroxy-16,16-difluoro-19-methyl-PGE₁)

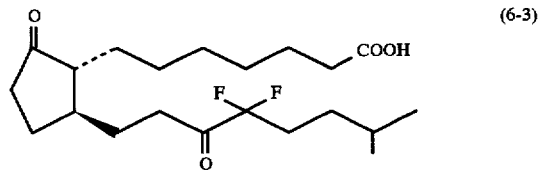
(6-3)

6-1: 7-[(1R,2R)-2-{(4,4-difluoro-7-methyl-3-oxooctyl}-5-oxocyclopent-3-enyl]heptanoic acid (6-2)

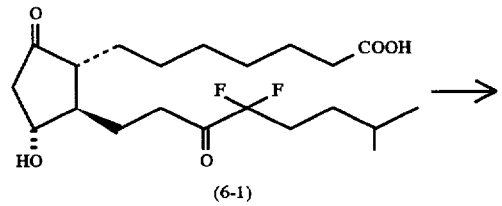
(6-1)

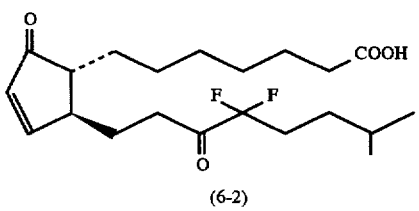
(6-2)

An acetic acid (10 ml) solution of 7-[(1R,2R,3R)-3-hydroxy-2-(4,4-difluoro-7-methyl-3-oxooctyl)-5-oxocyclopentyl]heptanoic acid (6-1) (0.533 g) prepared as described in Example 2 was heated overnight at 70° C. The crude product obtained after the usual work up was chromatographed on silica gel eluted with a mixed solvent of dichloromethane and methanol (20/1) to yield the compound (6-2).

Yield: 0.3969 g (77.9%)

6-2: 7-[(1R,2R)-2-(4,4-difluoro-7-methyl-3-oxooctyl]-5-oxocyclopentyl]heptanoic acid (6-3)

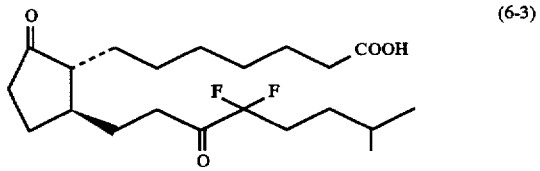
(6-3)

The compound (6-2) (0.533 g) in methanol was hydrogenated with 10% Pd on carbon (0.0281 g) under hydrogen atmosphere. The crude product was chromatographed on silica gel eluted with a mixed solvent of dichloromethane and methanol (20/1) to yield the compound (6-3).

Yield: 0.4576 g (81.0%)

n. m. r. (CDCl₃) δ: 0.92 (6H, d, J=6.0 Hz), 1.17–2.23 (22H, m), 2.34 (3H, t, J=7.5 Hz), 2.77 (2H, m).

mass m/z: 388 (M⁺)

EXAMPLE 7

7: Preparation of 7-[(1R,2R)-2-{4,4-difluoro-5(R),7-dimethyl-3-oxooctyl}-5-oxocyclopentyl]heptanoic acid (7-7) (13,14-dihydro-15-keto-11-dehydroxy-16,16-difluoro-17(R),19-dimethyl-PGE₁)

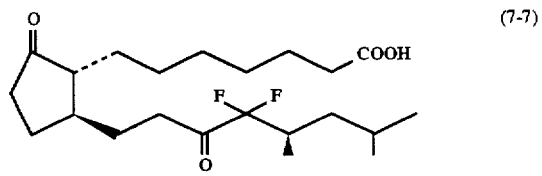
(7-7)

7-1: (1S,5R,6R,7R)-6-(t-butyldimethylsiloxymethyl)-7-(4-phenylbenzoyloxy)-2-oxabicyclo[3.3.0]octan-3-one (7-2)

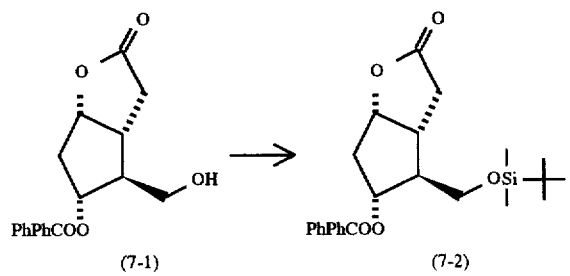
(7-1)    (7-2)

Corey lactone, (1S,5R,6R,7R)-6-(hydroxymethyl)-7-(4-phenylbenzoyloxy)-2-oxabicyclo[3.3.0]octan-3-one (7-1), (5.000 g) in DMF (7 ml) was treated with imidazole (2.9 g) and t-butyldimethylsilylchloride (4.28g) to yield the compound (7-2). 7-2: (1S,5R,6R,7R)-6-(t-butyldimethylsiloxymethyl)-7-hydroxy-2oxabicyclo[3.3.0]octan-3-one (7-3)

23

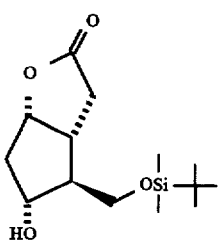
(7-3)

The compound (7-2) in methanol (40 ml) was converted to the compound (7-3) with potassium carbonate (3.920 g). The crude product was chromatographed on silica gel eluted with at mixed solvent of ethyl acetate and n-hexane (1/2) to yield the compound (7-3).

Yield: 3.196 g (78.6%)

7-3: (1S,5R,6R,7R)-6-(t-butyldimethylsiloxymethyl)
-7-(1-imidazolethiocarbonyloxy)-2-oxabicyclo
[3.3.0]octan-3-one (7-4)

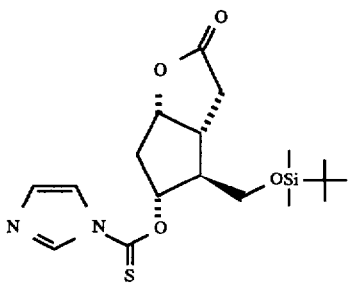
(7-4)

The compound (7-3) (2.500 g) in dichloromethane (20 ml) was treated with thiocarbonyldiimidazole (2.273 g) to yield the compound (7-4). The crude product was chromatographed on silica gel eluted with a mixed soluent of ethyl acetate and n-hexane (1/1).

Yield: 3.451 g (99.7%)

7-4: (1S,5R,6R)-6-(t-butyldimethylsiloxymethyl)-2-oxabicyclo[3.3.0]octan-3-one (7-5)

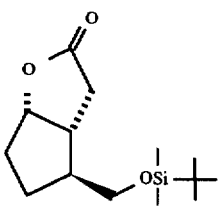
(7-5)

A solution of the compound (7-4) (3.450 g) in toluene was added dropwise to a solution of tributyltinhydride (5.06 g) in toluene (130 ml) while heated under reflux to yield the compound (7-5).

24

7-5: (1S,5R,6R)-6-(hydroxymethyl)-2-oxabicyclo
[3.3.0]octan-3-one (7-6)

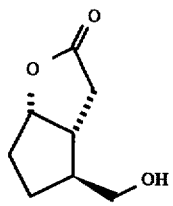
(7-6)

The compound (7-5) in THF (70 ml) was converted to the compound (7-6) with conc. hydrochloric acid (3.50 ml). The crude product was chromatographed on silica gel eluted with ethyl acetate.

Yield: 1.206 g (88.8 g)

7-6: (1S,5R,6R)-6-formyl-2-oxabicyclo[3.3.0]octan-
3-one (7-7)

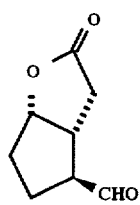
(7-7)

The compound (7-6) (1.200 g) was oxidized by means of Swern oxidation using oxalyl chloride (2.93 g) in dichloromethane (40 ml), DMSO (3.60 g), and triethylamine (6.22 g) to yield the compound (7-7).

Yield: 0.9109 g (76.9%)

7-7: (1S,5R,6R)-6-{E-4,4-difluoro-5(R),7-dimethyl-
3-oxooct-1-enyl}-2-oxabicyclo[3.3.0]octan-3-one
(7-8)

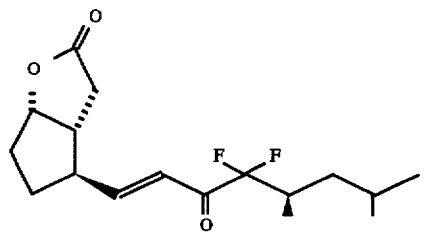
(7-8)

A solution of dimethyl {3,3-difluoro-4(R),6-dimethyl-2-oxoheptyl}phosphonate (7-9) (0.882 g) in THF (2.4 ml)

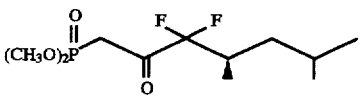
(7-9)

which was the identical one with the phosphonate (5-2) used in Example 5, prepared from the amide isomer having the shorter retention time when the two isomers of the amide generated from (dl)-2,2-difluoro-3,5-dimethylhexanoic acid and (R)-(+)-phenylethylamine were separated by means of normal phase chromatography, was treated by addition of a suspension of sodium hydride (63.8%, 0.1103 g) in THF (1.5 ml), followed by additoh of a solution of the compound (7-7) (0.5202 g) in THF (4 ml). The usual work up gave the compound (7-8).

Yield: 0.6651 g (72.1%)

7-8: (1S,5R,6R)-6-{4,4-difluoro-5(R),7-dimethyl-3-oxooctyl}-2-oxabicyclo[3.3.0]octan-3-one (7-10)

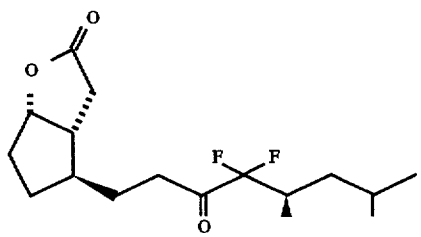
(7-10)

The compound (7-8) (0.6645 g) in ethanol was hydrogenated with 5% Pd on carbon and with hydrogen. The product was directly used in the next reaction without purification.

7-9: (1S,5R,6R)-2-{4,4-difluoro-5(R),7-dimethyl-3(RS)-hydroxyoctyl}-2-oxabicyclo[3.3.0]octan-3-one (7-11)

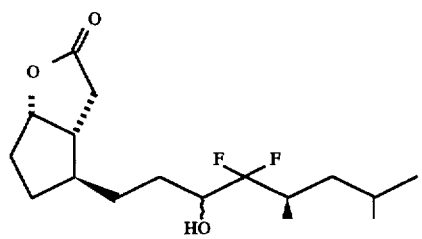
(7-11)

The compound (7-10) in methanol (14 ml) was treated at −40° C. with sodium borohydride (0.040 g). The crude product obtained after the usual work up was chromatographed on silica gel eluted with a mixed solvent of n-hexane and ethyl acetate (3/2) to yield the compound (7-11).

Yield: 0.6499 g (96.6%, for two reaction steps)

7-10: {(1S,3(RS),5R,6R)-6-{4,4-difluoro-5(R),7-dimethyl- 3(RS)-hydroxyoctyl}-2-oxabicyclo[3.3.0]octan-3-ol (7-12)

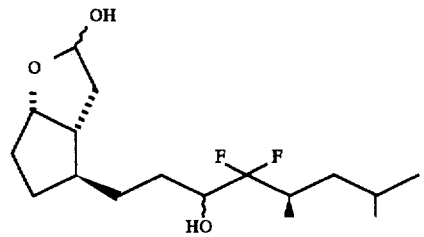
(7-12)

The compound (7-11) (0.6495 g) in toluene (3 ml) was treated at −78° C. with diisobutylaluminum hydride (1.5M toluene solution, 2.86 ml), the usual work up gave the compound (7-12).

7-11: Z-7-[(1R,2R,5S)-2-{4,4-difluoro-3(RS)-hydroxy-5(R),7-dimethyloctyl}-5-hydroxycyclopentyl]hept-5-enoic acid (7-13)

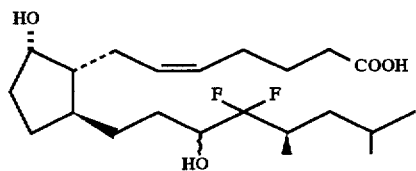
(7-13)

A THF (9 ml) solution of the compound (7-12) was added to the ylide generated from a suspension of (4-carboxybutyl) triphenylphosphonium bromide (3.16 g) in THF (9 ml) treated with potassium t-butoxide (1M THF solution, 14.3 ml) to yield the compound (7-13)

7-12: Benzyl Z-7-[(1R,2R,5S)-2-{4,4-difluoro-3(RS)-hydroxy-5(R),7-dimethyloctyl}-5-hydroxycyclopentyl]hept-5-enoate (7-14)

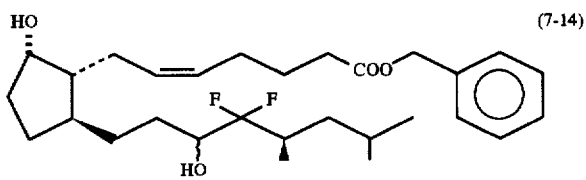
(7-14)

The compound (7-13) in acetonitrile (19 ml) was treated with benzyl bromide (1.57 g) and diisopropylamine (1.19 g) to yield the compound (7-14). The crude product obtained after the usual work up was chromatographed on silica gel.

Yield: 0.9257 g (91.7%)

7-13: Benzyl Z-7-[(1R,2R)-2-{4,4-difluoro-5(R),7-dimethyl-3-oxooctyl}-5-oxocyclopentyl]hept-5-enoate (7-15)

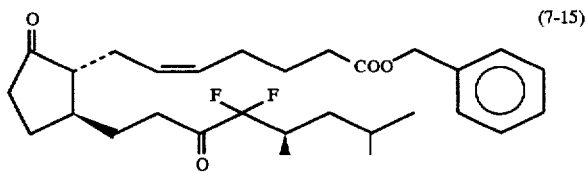
(7-15)

The compound (7-14) (0.9255 g) in dichloromethane (35 ml) was oxidized by means of Swern oxidation with using a solution of oxalyl chloride (1.19 g) in dichloromethane (20 ml), DMSO (1.46 g) and triethylamine (2.37 g). The crude product obtained after the usual work up was chromatographed on silica gel eluted with a mixed soluent of n-hexane and ethyl acetate (8/1).

Yield: 0.8701 (94.8%)

7-14: 7-[(1R,2R)-2-{4,4-difluoro-5(R),7-dimethyl-3-oxooctyl}-5-oxocyclopentyl]heptanoic acid (7-16)

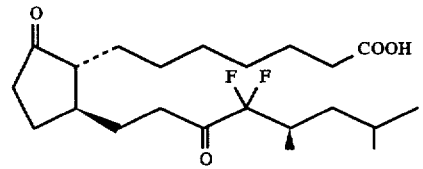
(7-16)

The compound (7-15) (0.8695 g) in ethanol (9 ml) was hydrogenated 10% Pd on carbon with hydrogen to yield the compound (7-16)

Yield: 0.5549 (77.8%)

n. m. r. (CDCl₃) δ: 0.86 (3H, d, J=6.6 Hz), 0.93 (3H, d, J=6.6 Hz), 0.98 (3H, d, J=7.1 Hz), 1.11–2.50 (22H,m), 2.34 (2H, t, J=7.6 Hz), 2.74 (2H, t, m), 7-9 (1H, br).

mass m/z: 402 (M⁺).

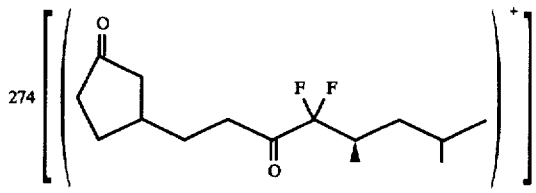

EXAMPLE 8

8: Preparation of 7-[(1R,2R,3R)-2-{4,4-difluoro-6(S)-methyl-3-oxooctyl}-3-hydroxy-5-oxocyclopentyl]heptanoic acid (7-8) (13,14-dihydro-15-keto-16,16-difluoro-18(S)-methyl-PGE₁)

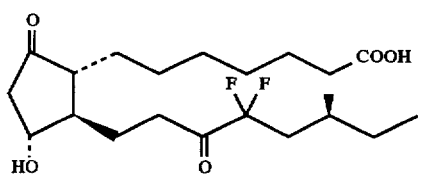

8-1: Ethyl 4(S)-methylhexanoate (8-2)

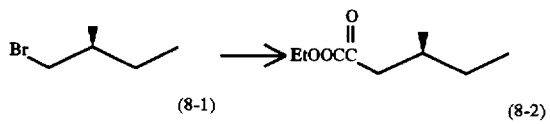

2S)-Methyl-1-butylmagnesium bromide was prepared from a solution of commercially available 2(S)-methyl-1-bromobutane (8-1) (10.0 g) in ethyl ether (10 ml) and Mg (1.61 g) in ethyl ether (20 ml). The generated Grignard reagent was let to react with diethyl oxalate (7.74 g) in diethyl ether to yield the compound (8-2).

Yield: 4.82 g (53%)

8-2: Ethyl 2,2-difluoro-4(S)-methyl-hexanoate (8-3)

The compound (8-2) (4.82 g) was converted with dimethylaminosulfurtrifluoride (4.1 ml) to the compound (8-3).

Yield: 4.13 g (76%), bp 66°–70° C./10 mmHg 8-3: Dimethyl {3,3-difluoro-5(S)-methyl-2-oxoheptyl}phosphonate (8-4)

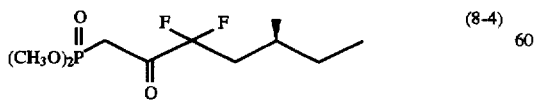

The compound (8-3) (4.09 g) was let to react with the phosphonate anion generated at −78° from dimethyl methylphosphonate (5.23 g) in THF (60 ml) and n-butyllithium (1.6M hexane solution, 25.8 ml). The crude product was chromatographed on silica gel eluted with a mixed soluent of ethyl acetate and hexane (7/3).

Yield: 4.66 g (81%)

8-4: 7-[(1R,2R,3R)-2-{4,4-difluoro-6(S)-methyl-3-oxooctyl}-3-hydroxy-5-oxocyclopentyl]heptanoic acid (8-6)

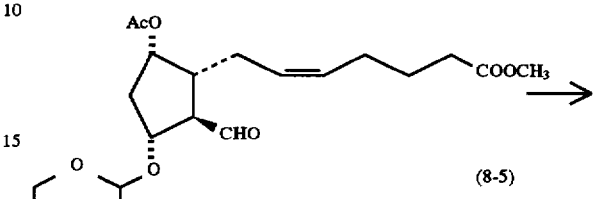

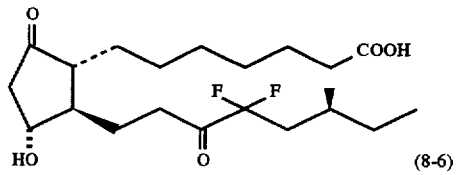

The compound (8-6) was prepared with using the aldehyde, methyl Z-7-[(1R,2R,3R,5S)-5-acetoxy-2-formyl-3-(tetrahydropyranyloxy)cyclopentyl]hept-5-enoate (8-5) and dimethyl{3,3-difluoro-5(S)-methyl-2-oxoheptyl}phosphonate (8-4) as described in Example 3 except that catalitic hydrogenation was not carried out.

n. m. r. (CDCl₃) δ: 0.89 (3H, t, J=7.6 Hz), 1.01 (3H, d, J=5.6 Hz), 1.12–2.14 (21H, m), 2.26 (1H, dd, J=17.7 Hz, J=10.1 Hz), 2.35 (2H, t, J=7.6 Hz), 2.58 (1H, dd, J=17.7 Hz, J=7.6 Hz), 4.18 (1H, m).

mass m/z: 404 (M⁺), 386 (M⁺–H2O).

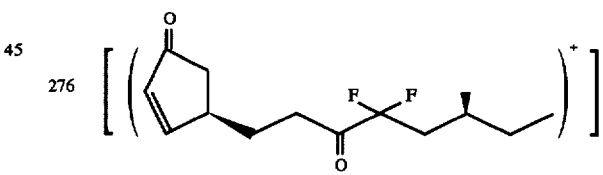

EXAMPLE 9

9: Preparation of 7-[(1 R,2R)-2-{4,4-difluoro-6(S)-methyl-3-oxooctyl}-5-oxocyclopentyl]heptanoic acid (9-3) (13,14-dihydro-15-keto-11-dehydroxy-16,16-difluoro-18(S)-methyl-PGE₁)

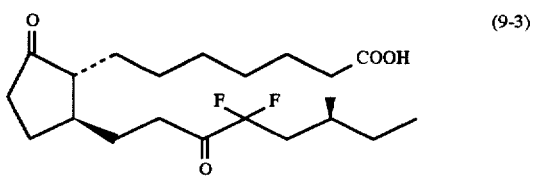

9-1: Benzyl 7-[(1R,2R)-2-{4,4-difluoro-6(S)-methyl-3-oxooctyl}-5-oxocyclopent-3-enyl]heptanoate (9-2)

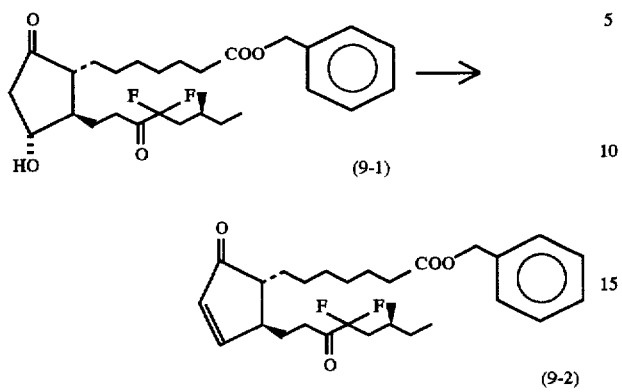

A solution of the synthetic intermediate obtained in Example 8, benzyl 7-[(1R,2R,3R)-2-{4,4-difluoro-6(S)-methyl-3-oxooctyl}-3-hydroxy-5-oxocyclopentyl}heptanoate (9-1) (0.466 g) in acetic acid (15 ml) was heated at 70°–80° C. for 20 hours to yield the compound (9-2). The crude product was chromatographed on silica gel eluted with a mixed solvent of ethyl acetate and hexane (1/4).

Yield: 0.399 g (79%)

9-2: 7-[(1R,2R)-2-{4,4-difluoro-6(S)-methyl-3-oxooctyl}-5-oxocyclopentyl]heptanoic acid (9-3)

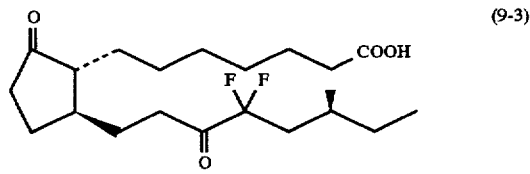

The compound (3) (0.399 g) in ethanol (20 ml) was hydrogenated with 5% Pd on carbon under hydrogen atmosphere. The product was chromatographed on silica gel to yield the compound (9-3).

Yield: 0.260 g (80%)

n. m. r. (CDCl3) δ: 0.90 (3H, t, J=7.6 Hz), 0.98 (3H, d, J=6.6 Hz), 1.13–2.50 (23H, m), 2.35 (2H, t, J=7.6 Hz), 2.73 (2H, m).

mass m/z: 388 (M⁺).

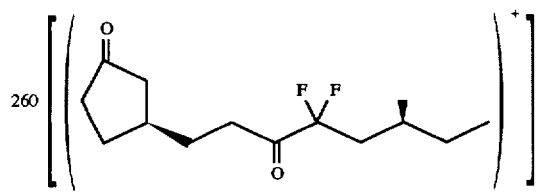

EXAMPLE 10

10: Preparation of 7-[(1R,2R)-2-{4,4-difluoro-5(R)-methyl-3-oxooctyl}-5-oxocyclopentyl]heptanoic acid (10-3) (13,14-dihydro-15-keto-11-dehydroxy-16,16-difluoro-17(R)-methyl-PGE₁)

10-1: 7-[(1R,2R)-2-{4,4-difluoro-5(R)-methyl-3-oxooctyl}-5-oxocyclopentyl]heptanoic acid (10-3)

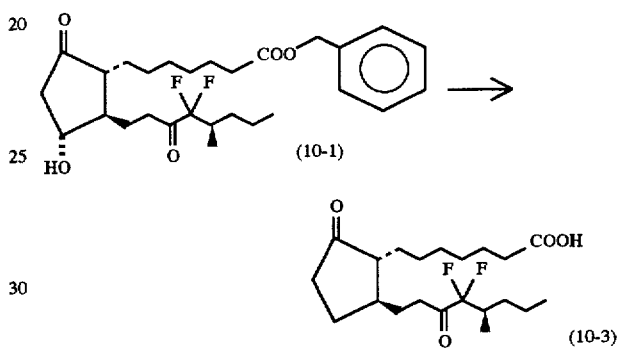

The compound prepared as described in Example 3, benzyl 7-[(1R,2R,3R)-2-{4,4-difluoro-5(R)-methyl-3-oxooctyl}-3-hydroxy-5-oxocyclopentyl]heptanoate (10-1), which was the identical one with the compound (3-9) in Example 3, was converted to the colorless oily material (10-3) as carried out as Example 9.

n. m. r. (CDCl₃) δ: 0.92 (3H, t, J=6.6 Hz), 1.00 (3H, d, J=6.6 Hz), 1.08–2.50 (23H, m), 2.34 (2H, t, J=7.6 Hz), 2.74 (2H, m).

mass m/z: 388 (M⁺).

EXAMPLE 11

11-1: Preparation of 7-[(1R,2R,3R)-2-{4,4-difluoro-5(S), 7-dimethyl-3-oxooctyl}-3-hydroxy-5-oxocyclopentyl}heptanoic acid (11-1) (13,14-dihydro-15-keto-16,16-difluoro-17(S),19-dimethyl-PGE₁)

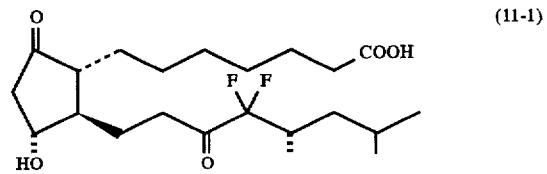

The compound (11-1) was prepared as Example 5 except for using dimethyl{3,3-difluoro-4(S), 6-dimethyl-2-oxoheptyl}phosphonate (11-2);

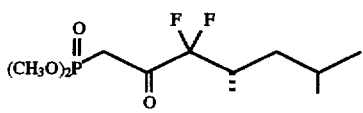

prepared from the amide isomer having the longer retention time when the two isomers of the amine generated from (dl)-2,2-difluoro-3,5-dimethylhexanoic acid and (R)-(+)-phenylethylamine by means of normal phase chromatography.

n. m. r. (CDCl$_3$) δ: 0.86 (3H, d, J=6.6 Hz), 0.94 (3H, d, J=6.6 Hz), 0.98 (2H, d, J=7.1 Hz), 1.08 (1H, d, J=7.1 Hz), 1.16–2.48 (21H, m), 2.35 (2H, t, J=7.6 Hz), 2.50–2.80 (1H, m), 2.92 (1H, br), 4.05–4.30 (1H, m), 5.5–7.5 (1H, br).

mass m/z: 418 (M$^+$), 400 (M$^+$-H$_2$O),

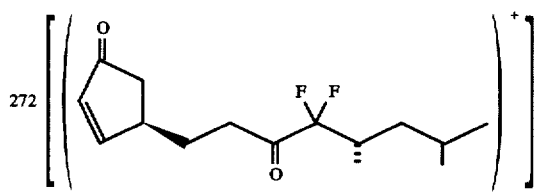

EXAMPLE 12

12-1: Preparation of 7-[(1R,2R)-2-{4,4-difluoro-5(S), 7-dimethyl-3-oxooctyl}-5-oxocyclopentyl]heptanoic acid (12-2) (13,14-dihydro-15-keto-11-dehydroxy-16,16-difluoro-17(S),19-dimethyl-PGE$_1$)

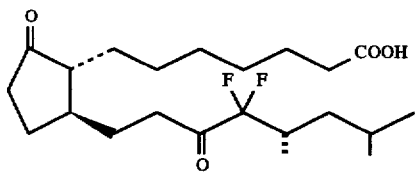

The compound (12-2) was prepared as described in Example 9 and 10 with using the compound (11-1) obtained in Example 11.

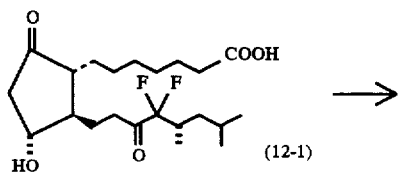

n. m. r. (CDCl$_3$) δ: 0.86 (3H, d, J=6.6 Hz), 0.94 (3H, d, J=6.6 Hz), 0.98 (3H, d, J=7.1 Hz), 1.11–2.50 (22H, m), 2.34 (2H, t, J=7.6 Hz), 2.75 (2H, m), 8–10 (1H, br).

mass m/z: 402 (M$^+$),

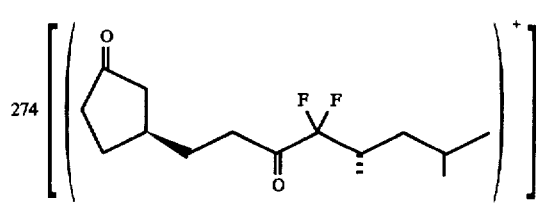

EXAMPLE 13

13: Preparation of 7-[(1R,2R,3R)-2-(4,4-difluoro-6,6-dimethyl-3-oxooctyl)-3-hydroxy-5-oxocyclopentyl]heptanoic acid (13-(13,14-dihydro-15-keto-16,16-difluoro-18,18-dimethyl-PGE$_1$)

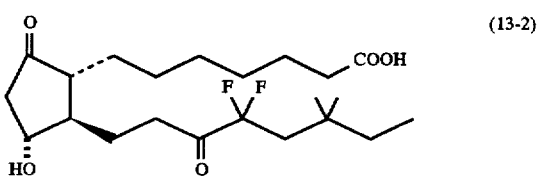

The compound (13-2) was prepared as described in Example 3 except for using dimethyl(3,3-difluoro-5,5-dimethyl-2-oxoheptyl)phosphonate (13-1).

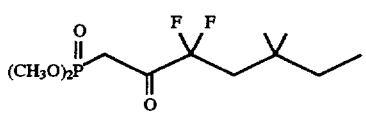

n. m. r. (CDCl$_3$) δ: 0.84 (3H, t, J=7.1 Hz), 1.01 (6H, s), 1.13–2.12 (21H, m), 2.25 (1H, dd, J=17.7 Hz, J=11.6 Hz), 2.34 (2H, t, J=7.6 Hz), 2.68 (1H, dd, J=11.6 Hz, J=6.6 Hz), 4.17 (1H, m).

EXAMPLE 14

Preparation of 7-[(1R,2R,3R)-2-(4,4-difluoro-6-ethyl-3-oxooctyl)-3-hydroxy-5-oxocyclopentyl]heptanoic acid (14-2) (13,14-dihydro-15-keto-16,16-difluoro-18-ethyl-PGE$_1$)

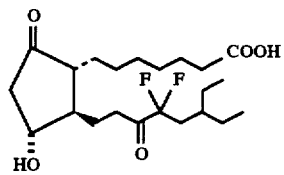

The compound (14-2) was prepared as described in Example 3 except for using dimethyl (3,3-difluoro-5-ethyl-2-oxoheptyl)phosphonate (14-1).

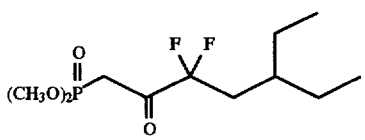

n. m. r. (CDCl$_3$) δ: 0.86 (3H, t, J=7.1 Hz), 1.2–2.1 (23H, m), 2.25 (1H, dd, J=17.7 Hz, J=11.1 Hz), 2.33 (2H, t, J=6.6 Hz), 2.58 (1H, dd, J=17.7 Hz, J=6.6 Hz), 4.18 (1H, m).

mass m/z: 418 (M⁺), 400 (M⁺–H₂O), 382 (M⁺-2H₂O),

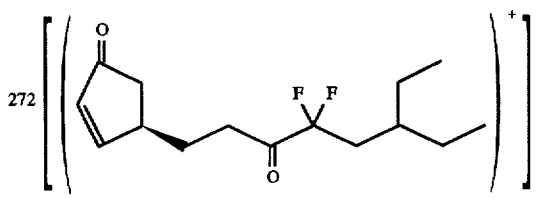

EXAMPLE 15

Preparation of 7-[(1R,2R,3R)-2-(4,4-difluoro-6-methyl-3-oxoheptyl)-3-hydroxy-5-oxocyclopentyl] heptanoic acid (15-9) (13,14-dihydro-15-keto-16,16-difluoro-18-methyl-20-nor-PGE₁)

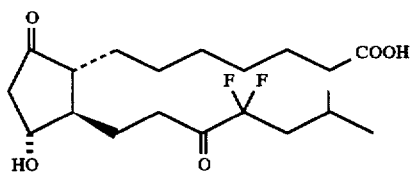

15-1: (1S,5R,6R,7R)-6-{E-4,4-difluoro-3(RS)-hydroxy-6-methylhept-1-enyl}-7-(tetrahydropyranyloxy)-2-oxabicyclo[3.3.0]octan-3-one (15-3)

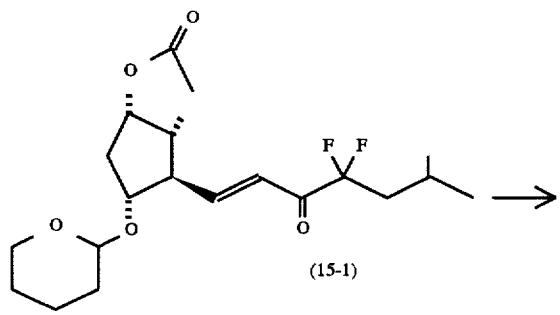

(1S,5R,6R,7R)-6-{E-4,4-difluoro-6-methyl-3-oxohept-1-enyl)-7-(tetrahydropyranyloxy)-2-oxabicyclo[3.3.0]octan-3-one (15-1) (2.285 g) prepared as described in Example 1 except for using dimethyl(3,3-difluoro-5-methyl-2-oxohexyl)phosphonate (15-2), was treated with sodium borohydride in methanol (50 ml) under the presence of cesium chloride 7 hydrate to yield the compound (15-3).

Yield: 1.989 g (86.6%)

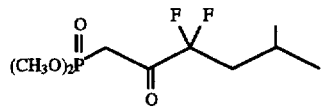

15-2: {1S,3(RS),5R,6R,7R}-6-{E-4,4-difluoro-3(RS)-hydroxy-6-methylhept-1-enyl}-7-(tetrahydropyranyloxy)-2-oxabicyclo[3.3.0]octan-3-ol (15-4)

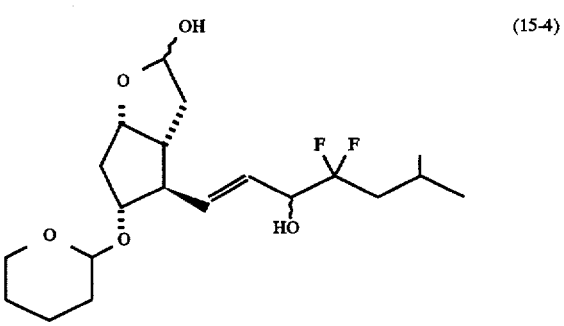

The compound (15-3) (1.989 g) was treated with diisobutylaluminum hydride in toluene (40 ml) to yield the compound (15-4).

15-3:Z-7-[(1R,2R,3R,5S)-2-{E-4,4-difluoro-3(RS)-hydroxy-6-methylhept-1-enyl}-5-hydroxy-3-(tetrahydropyranyloxy)cyclopentyl]hept-5-enoic acid (15-5)

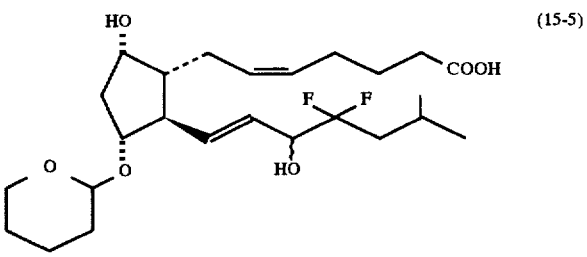

A THF solution of the compound (15-4) was added to the ylide generated from (4-carboxybutyl)triphenylphosphonium bromide (7.490 g) in THF treated with potassium t-butoxide (1M THF solution, 33.8 ml) to yield the compound (15-5).

15-4: Benzyl Z-7-[(1R,2R,3R,5S)-2-{E-4,4-difluoro-3(RS)-hydroxy-6-methylhept-1-enyl}-5-hydroxy-3-(tetrahydropyranyloxy)cyclopentyl]hept-5-enoate (15-6)

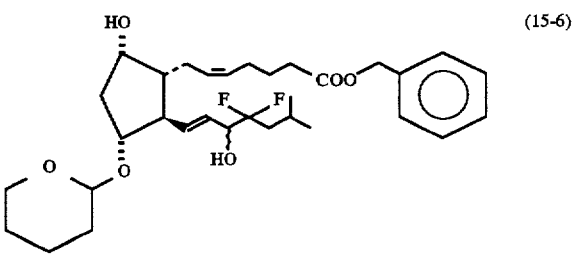

The compound (15-5) in acetonitrile (30 ml) was treated with benzyl bromide (1.83 ml) and diisopropylamine (2.68 ml) to yield the compound (15-6).

Yield: 1.613 g (55.8%, for the two reaction steps)

15-5: Benzyl Z-7-[(1R,2R,3R,5S)-2-(E-4,4-difluoro-6-methyl-3-oxohept-1-enyl)-5-oxo-3-(tetrahydropyranyloxy)cyclopentyl]hept-5-enoate (15-7)

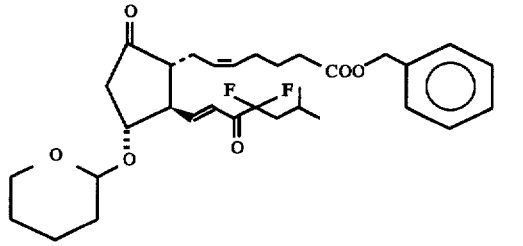
(15-7)

The compound (15-6) (1.613 g) was oxidized by means of Swern oxidation with using a diluted solution of oxalyl chloride (2M dichloromethan solution, 7.14 ml) in dichloromethane (70 ml), DMSO (2.47 ml) and triethylamine (2.4 ml).

Yield: 1.218 g (76.1%)

15-6: Benzyl Z-7-[(1R,2R,3R,5S)-2-(E-4,4-difluoro-6-methyl-3-oxohept-1 -enyl)-3-hydroxy-5-oxocyclopentyl]hept-5-enoate (15-8)

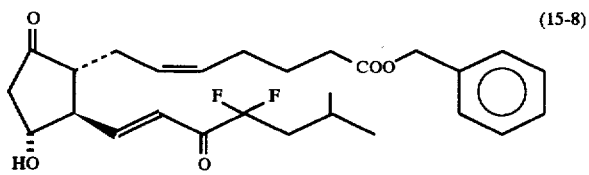
(15-8)

The compound (15-7) (1.150 g) in a mixed soluent of acetic acid, THF, and water (3/1/1) was heated at 50° C. for 2 hours to yield the compound (15-8).

Yield: 0.812 g (83.1%)

15-7: 7-[(1R,2R,3R,5S)-2-(4,4-difluoro-6-methyl-3-oxoheptanyl)-3-hydroxy-5-oxocyclopentyl]heptanoic acid (15-9)

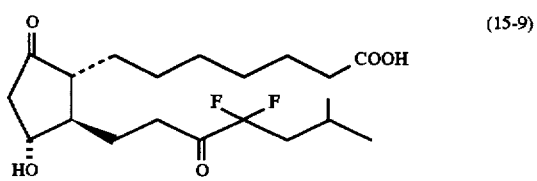
(15-9)

The compound (15-8) (0.739 g) in ethyl acetate (30 ml) was hydrogenated with 5% Pd on carbon under hydrogen atmosphere to yield the compound (15-9).

Yield: 0.5053 g (83.4%)

n. m. r. (CDCl$_3$) δ: 1.00 (6H, d, J=6.1 Hz), 1.2–2.15 (20H, m), 2.24 (1H, dd, 17.7 Hz, J=11.6 Hz), 2.33 (2H, t, J=7.1 Hz), 2.56 (1H, dd, J=17.7 Hz, J=6.6 Hz), 4.17 (1H, m).

mass m/z: 390 (M$^+$), 354 (M$^+$–2H$_2$O),

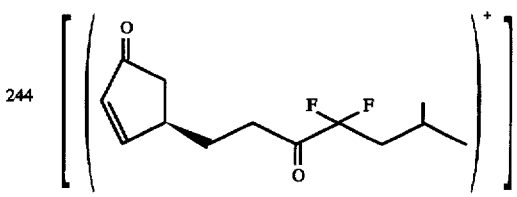

EXAMPLE 16

16: Preparation of 7-[(1R,2R,3R)-2-{4,4-difluoro-6(R)-methyl-3-oxooctyl}-3-hydroxy-5-oxocyclopentyl]heptanoic acid (16-2) (13,14-dihydro-15-keto-16,16-difluoro-18(R)-methyl-PGE$_1$)

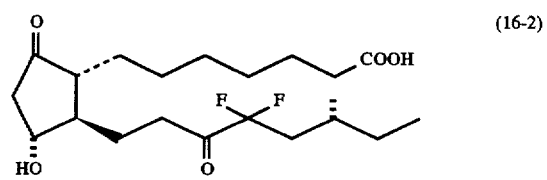
(16-2)

The compound (16-2) was prepared as described in Example 8 except for using dimethyl{3,3-difluoro-5(R)-methyl-2-oxoheptyl}phosphonate (16-1) prepared from (R)-2-methylbutanol.

n. m. r. (CDCl$_3$) δ: 0.90 (3H, t, J=7.1 Hz), 1.00 (3H, d, J=6.6 Hz), 1.15–2.15 (22H, m), 2.25 (1H, dd, J=17.7 Hz, J=11.1 Hz), 2.35 (2H, t, J=6.6 Hz), 2.58 (1H, dd, J=17.7 Hz, J=6.6 Hz), 4.18 (1H, m).

mass m/z : 404 (M$^+$), 386 (M$^+$–H$_2$O), 368 (M$^+$–2H$_2$O),

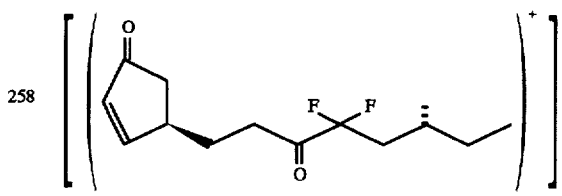

EXAMPLE 17

17: Preparation of 7-[(1R2R,3R)-2-(4,4-difluoro-8-methyl-3-oxononyl)-3-hydroxy-5-oxocyclopentyl] heptanoic acid (17-2) (13,14-dihydro-15-keto-16,16-difluoro-20,20-dimethyl-PGE$_1$)

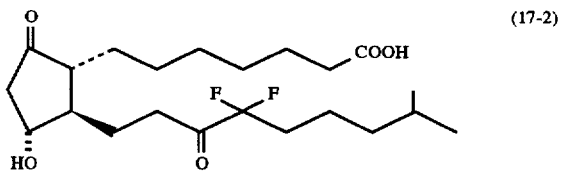
(17-2)

The compound (17-2) was prepared as described in Example 3 except for using dimethyl(3,3-difluoro-7-methyl-2-oxooctyl)phosphonate (17-1).

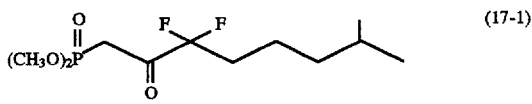

n. m. r. (CDCl₃) δ: 0.90 (6H, d, J=6.1 Hz), 1.15–2.15 (23H, m), 2.24 (1H, dd, J=17.7 Hz, J=11.1 Hz), 2.36 (2H, t, J=6.6 Hz), 2.59 (1H, dd, J=17.7 Hz, J=6.6 Hz), 4.18 (1H, m).

mass m/z: 502 (M⁺), 484 (M⁺–H₂O),

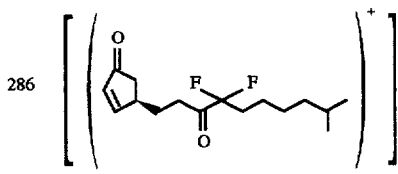

EXAMPLE 18

18: Preparation of 7-[(1R,2R)-2-(4,4-difluoro-8-methyl-2-oxononyl)-5-oxocyclopentyl]heptanoic acid (18-1) (13,14-dihydro-15-keto-11-dehydroxy-16,16,-difluoro-20,20-dimethyl-PGE₁)

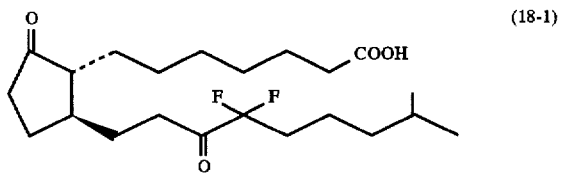

The compound (18-1) was prepared as described in Example 6 with using the compound (17-2) prepared in Example 17.

n. m. r. (CDCl₃) δ: 0.89 (6H, d, J=6.6 Hz), 1.15–2.25 (27H, m), 2.36 (,2H, t, J=7.1 Hz), 2.78 (1 H, m).

EXAMPLE 19

Preparation of 7-[(1R,2R)-2-{4,4-difluoro-6(R)-methyl-3-oxooctyl}-5-oxocyclopentyl]heptanoic acid (19-2) (13,14-dihydro-15-keto-11-dehydroxy-16,16-difluoro-18(R)-methyl-PGE₁)

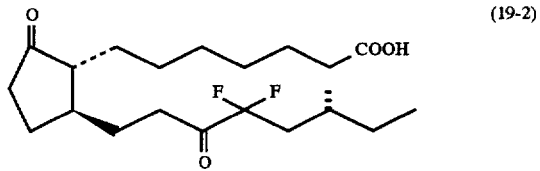

The compound was prepared as described in Example 6 with using the synthetic intermediate, benzyl 7-[(1R,2R,3R)-2-{4,4-difluoro-6(R)-methyl-3-oxooctyl}-3-hydroxy-5-oxocyclopentyl]heptanoate (19-1) obtained in Example 16.

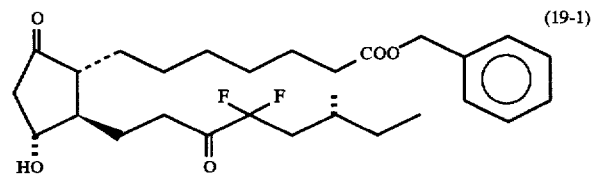

n. m. r. (CDCl₃) δ: 0.88 (3H, t, J=7.1 Hz), 0.97 (3H, d, J=6.1 Hz), 1.1–2.25 (25H, m), 2.34 (2H, t, J=6.6 Hz), 2.76 (1H, m).

mass m/z: 404 (M⁺), 386 (M⁺–H₂O), 368 (M⁺–2H₂O).

Test Example 1

Crj: Wister rats (7 weeks old, weight: 220–250 g) were kept without food for 16 hours, and hydrochloric acid-D-galactosamine 800 mg/kg was administrated by intra peritonealy injection in order to elicit acute hepatopathy model. After 24 hours from the administration of galactosamine, blood sample was collected under ether anesthesia and a serum was separated. The serum was assayed for serum biochemical profile of liver function test by an automatic analyzer (AU 550 available Orympus Kogaku Kogyo K.K.).

Test compound was dissolved in 0.5% ethanol physiological saline, which was orally administered by force using an oral sonde for rat at 30 minutes before, 2 hours and 6 hours after the administration of the galactosamine.

The following four items were tested for the serum biochemical liver function test:

glutamic oxaloacetic transaminase (GOT), glutamic pyruvic transaminase (GPT)

lactate dehydrogenase (LDH)

total bilirubin (T-Bil)

The inhibiting Ratio (%) was obtained by the results of the serum biochemical profile of liver functional test how much the increases in the above four items by the administration of galactosamine was inhibited by the test compounds. The Inhibiting, Ratio (%) was calculated by the following equation:

$$\left\{ 1 - \left( \frac{\text{administrated rats} - \text{nomal control rats}}{\text{model control rats} - \text{nomal control rats}} \right) \right\} \times 100$$

(All of the data in the equation are represented by average)

The generation of a diarrhea and a loose feces observed up to 2 hours after the 3rd administration of the test compounds, and the number of the rats having diarrhea or loose feces were recorded.

TABLE 1

| test compound | dose (μg/kg × 3) | number (n) | inhibiting ratio (%) | | | | diarrhea loose feces |
|---|---|---|---|---|---|---|---|
| | | | GOT | GPT | LDH | T-Bil | |
| 1 | 30 | 10 | 28 | 42 | 22 | 82 | 3/10 diarrhea |
| 2 | 30 | 10 | 29 | 36 | 32 | 51 | non |

Test Compound 1:

13,14-dihydro-15-keto-16,16-difluoro-PGE₂ (compound set forth in Publn. A),

Test Compound 2:

13,14-dihydro-15-keto-16,16-difluoro-19-methyl-PGE₂ (compound prepared in the Synthetic Example 1)

As apparent from the above Table 1 in the Test Compound 1, known compound, diarrhea was observed in 3/10 rats for the dose of 30 μg/kg, whereas in the Test Compound 2 of the present invention no diarrhea was observed in every rat for the same condition. Therefore, the diarrhea which is a side effect of the Test Compound 1 was apparently separated from the Test Compound 2.

Test Example 2

This test was carried out according the same manner as in the Example 1 providing the following compounds were used as test compounds.

The results were shown in Table 2.

TABLE 2

| test compound | dose (μg/kg × 3) | number (n) | inhibiting ratio (%) | | | | diarrhea loose feces |
|---|---|---|---|---|---|---|---|
| | | | GOT | GPT | LDH | T-Bil | |
| 3 | 100 | 6 | 63 | 76 | 61 | 80 | 1/6 diarrhea; 2/6 loose feces |
| 4 | 100 | 6 | 54 | 57 | 51 | 89 | non |
| 5 | 100 | 6 | 51 | 66 | 59 | 72 | non |

Test Compound 3:

13,14-dihydro-15-keto-16,16-difluoro-PGE$_1$ (compound set forth in the Publn. A).

Test Compound 4:

13,14-dihydro-15-keto-16,16-difluoro-17(R)-methyl-PGE$_1$ (compound prepared in Synthetic Example 3).

Test Compound 5:

13,14-dihydro-15-keto-16,16-difluoro-19-methyl-PGE$_1$ (compound prepared in Synthetic Example 2)

As apparent from the above results in the Test Compound 3, known compound, the diarrhea and loose feces were observed in 1/6 rat and in 2/6 rats respectively for 100 μg/kg administration. In the Test Compounds 4 and 5 of the present invention have no diarrhea in any cases. Therefore, the diarrhea which is a side effect of the Test Compound 3 was apparently separated from the Test Compounds 4 and 5.

Test Example 3

This test was carried out according the same manner as in the Example 1 using the following compounds as test compounds.

The results were shown in Table 3.

TABLE 3

| test compound | dose (μg/kg × 3) | number (n) | inhibiting ratio (%) | | | | diarrhea loose feces |
|---|---|---|---|---|---|---|---|
| | | | GOT | GPT | LDH | T-Bil | |
| 6 | 1000 | 8 | 60 | 71 | 63 | 88 | non |
| 7 | 1000 | 8 | 52 | 63 | 62 | 86 | non |
| 8 | 1000 | 5 | 59 | 56 | 63 | 92 | non |

Test Compound 6:

13,14-dihydro-15-keto-16,16-difluoro-17 (R),19-dimethyl-PGE$_1$ (compound prepared in Synthetic Example 5).

Test Compound 7:

13,14-dihydro-15-keto-11-dehydroxy-16,16-difluoro-19-methyl-PGE$_1$ (compound prepared in Synthetic Example 6).

Test Compound 8:

13,14-dihydro-15-keto-16,16-difluoro-17(S)-methyl-PGE$_1$ (compound prepared in Synthetic Example 4)

As apparent from the above results in the Test Compounds 6, 7 and 8 of the present invention have no diarrhea for 1000 μg/kg in any cases. Therefore, the diarrhea which is a side effect of known Compounds is apparently separated in the Test Compounds 6, 7 and 8.

Test Example 4

This test was carried out according the same manner as in the Example 1 excepting the following compounds were used as test compounds.

The results were shown in Table 4.

TABLE 4

| test compound | dose (μg/kg × 3) | number (n) | inhibiting ratio (%) | | | diarrhea loose feces |
|---|---|---|---|---|---|---|
| | | | GOT | GPT | T-Bil | |
| 9 | 100 | 7 | 44 | 54 | 80 | non |
| 9 | 1000 | 7 | 84 | 88 | 95 | non |
| 10 | 100 | 7 | 36 | 39 | 59 | non |

Test Compound 9:

13,14-dihydro-15-keto-16,16-difluoro-18(S)-methyl-PGE$_1$ (compound prepared in Synthetic Example 8).

Test Compound 10:

13,14-dihydro-15-keto-11-dehydroxy-16,16-difluoro-17 (R)-methyl-PGE$_1$ (compound prepared in Synthetic Example 10).

Test Example 5

This test was carried out according the same manner as in the Example 1 excepting the following compounds were used as test compounds.

The results were shown in Table 5.

TABLE 5

| test compound | dose (μg/kg × 3) | number (n) | inhibiting ratio (%) | | | diarrhea loose feces |
|---|---|---|---|---|---|---|
| | | | GOT | GPT | T-Bil | |
| 11 | 10 | 16 | 45 | 34 | 56 | non |
| 12 | 100 | 7 | 38 | 40 | 69 | non |
| 13 | 10 | 7 | 47 | 42 | 75 | non |

Test Compound 11:

13,14-dihydro-15-keto-16,16-difluoro-18(R)-methyl-PGE$_1$ (compound prepared in Synthetic Example 16).

Test Compound 12:

13,14-dihydro-15-keto-16,16-difluoro-18-methyl-20-nor-PGE$_1$ (compound prepared in Synthetic Example 15).

Test Compound 13:

13,14-dihydro-15-keto-16,16-difluoro-18-ethyl-PGE$_1$ (compound prepared in Synthetic Example 14).

The PG derivatives of the present invention exhibit improvement in the disorder of hepatocytes to the similar level to that of concretely known compounds having a linear ω-chain, and additionally the side effects such as diarrhea are apparently separated. These effects cannot be predicted from the prior arts.

What is claimed is:

1. A pharmaceutical composition for comprising an effective amount of the compound represented by the formula (I):

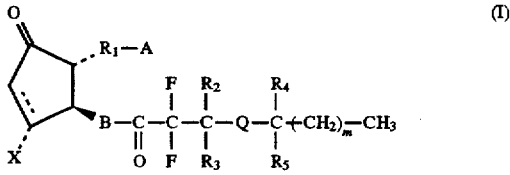

wherein A is —COOH, pharmaceutically acceptable salts thereof or esters which can be hydrolyzed by an esterase;

B is —CH$_2$—CH$_2$— or —CH=CH—,

X is a hydrogen atom or a hydroxyl group provided that X is a hydrogen atom when the cyclopentyl group has a double bond;

R₁ is a divalent saturated or unsaturated C₆ aliphatic hydrocarbon group;

R₂, R₃, R₄, R₅ are independently a hydrogen atom, a methyl group or an ethyl group provided at least one of them is a methyl group or an ethyl group;

Q is a single bond or a saturated C₁–C₆ aliphatic hydrocarbon group which may have a branch; and m is 0 or 1 and a pharmaceutically acceptable carrier.

2. The pharmaceutical composition according to claim 1 wherein the compound represented by the formula I is 13,14-dihydro-15-keto-16,16-difluoro-19-methyl-PGE, pharmaceutically acceptable salts thereof or esters hydrolyzable by an esterase.

3. The pharmaceutical composition according to claim 1 wherein the compound represented by the formula I is 13,14-dihydro-15-keto-16,16-difluoro-17-methyl-PGE, pharmaceutically acceptable salts thereof or esters hydrolyzable by an esterase.

4. The pharmaceutical composition according to claim 1 wherein the compound represented by the formula I is 13,14-dihydro-15-keto-16,16-difluoro-17,19-dimethyl-PGE, pharmaceutically acceptable salts thereof or esters hydrolyzable by an esterase.

5. The pharmaceutical composition according to claim 1 wherein the compound represented by the formula I is 13,14-dihydro-5-keto-16,16-difluoro-18-methyl-PGE, pharmaceutically acceptable salts thereof or esters hydrolyzable by an esterase.

6. The pharmaceutical composition according to claim 1 wherein the compound represented by the formula I is 13,14-dihydro-15-keto-16,16-difluoro-18,18-dimethyl-PGE, pharmaceutically acceptable salts thereof or esters hydrolyzable by an esterase.

7. The pharmaceutical composition according to claim 1 wherein the compound represented by the formula I is 13,14-dihydro-15-keto-16,16-difluoro-18-ethyl-PGE, pharmaceutically acceptable salts thereof or esters hydrolyzable by an esterase.

8. The pharmaceutical composition according to claim 1 wherein the compound represented by the formula I is 13,14-dihydro-15-keto-16,16-difluoro-18-methyl-20-nor-PGE, pharmaceutically acceptable salts thereof or esters hydrolyzable by an esterase.

9. The pharmaceutical composition according to claim 1 wherein the compound represented by the formula I is 13,14-dihydro-15-keto-16,16-difluoro-20,20-methyl-PGE, pharmaceutically acceptable salts thereof or esters hydrolyzable by an esterase.

10. The pharmaceutical composition according to claim 1 wherein the compound represented by the formula I is 13,14-dihydro-15-keto-11-dehydroxy-16,16-difluoro-19-methyl-PGE, pharmaceutically acceptable salts thereof or esters hydrolyzable by an esterase.

11. The pharmaceutical composition according to claim 1 wherein the compound represented by the formula I is 13,14-dihydro-15-keto-11-dehydroxy-16,16-difluoro-17-methyl-PGE, pharmaceutically acceptable salts thereof or esters hydrolyzable by an esterase.

12. The pharmaceutical composition according to claim 1 wherein the compound represented by the formula I is 13,14-dihydro-15-keto-11-dehydroxy-16,16-difluoro-17,19-dimethyl-PGE, pharmaceutically acceptable salts thereof or esters hydrolyzable by an esterase.

13. The pharmaceutical composition according to claim 1 wherein the compound represented by the formula I is 13,14-dihydro-15-keto-11-dehydroxy-16,16-difluoro-18-methyl-PGE, pharmaceutically acceptable salts thereof or esters hydrolyzable by an esterase.

14. The pharmaceutical composition according to claim 1 wherein the compound represented by the formula I is 13,14-dihydro-15-keto-11-dehydroxy-16,16-difluoro-20,20-dimethyl-PGE, pharmaceutically acceptable salts thereof or esters hydrolyzable by an esterase.

15. A compound represented by formula I:

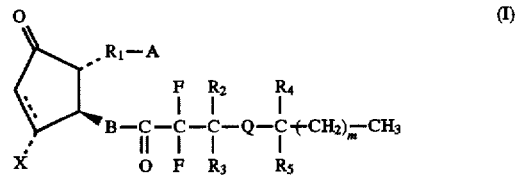

wherein A is —COOH, pharmaceutically acceptable salts thereof or esters which can be hydrolyzed by an esterase;

B is —CH₂—CH₂— or —CH=CH—,

X is a hydrogen atom or a hydroxyl group provided that X is a hydrogen atom when the cyclopentyl group has a double bond;

R₁ is a divalent saturated or unsaturated C₆ aliphatic hydrocarbon residue;

R₂, R₃, R₄ and R₅ are independently a hydrogen atom, a methyl group or an ethyl group provided at least one of them is a methyl group or an ethyl group;

Q is a single bond or a saturated C₁–C₆ aliphatic hydrocarbon group which may have a branch; and m is 0 or 1.

16. The compound of claim 15 being 13,14-dihydro-15-keto-16,16-difluoro-19-methyl-PGE, pharmaceutically acceptable salts thereof or esters hydrolyzable by an esterase.

17. The compound of claim 15 being 13,14-dihydro-15-keto-16,16-difluoro-17-methyl-PGE, pharmaceutically acceptable salts thereof or esters hydrolyzable by an esterase.

18. The compound of claim 15 being 13,14-dihydro-15-keto-16,16-difluoro-17,19-dimethyl-PGE, pharmaceutically acceptable salts thereof or esters hydrolyzable by an esterase.

19. The compound of claim 15 being 13,14-dihydro-15-keto-16,16-difluoro-18-methyl-PGE, pharmaceutically acceptable salts thereof or esters hydrolyzable by an esterase.

20. The compound of claim 15 being 13,14-dihydro-15-keto-16,16-difluoro-18,18-dimethyl-PGE, pharmaceutically acceptable salts thereof or esters hydrolyzable by an esterase.

21. The compound of claim 15 being 13,14-dihydro-15-keto-16,16-difluoro-18-ethyl-PGE, pharmaceutically acceptable salts thereof or esters hydrolyzable by an esterase.

22. The compound of claim 15 being 13,14-dihydro-15-keto-16,16-difluoro-18-methyl-20-nor-PGE, pharmaceutically acceptable salts thereof or esters hydrolyzable by an esterase.

23. The compound of claim 15 being 13,14-dihydro-15-keto-16,16-difluoro-20,20-methyl-PGE, pharmaceutically acceptable salts thereof or esters hydrolyzable by an esterase.

24. The compound of claim 15 being 13,14-dihydro-15-keto-11-dehydroxy-16,16-difluoro-19-methyl-PGE, pharmaceutically acceptable salts thereof or esters hydrolyzable by an esterase.

25. The compound of claim 15 being 13,14-dihydro-15-keto-11-dehydroxy-16,16-difluoro-17-methyl-PGE, pharmaceutically acceptable salts thereof or esters hydrolyzable by an esterase.

26. The compound of claim 15 being 13,14-dihydro-15-keto-11-dehydroxy-16,16-difluoro-17,19-dimethyl-PGE, pharmaceutically acceptable salts thereof or esters hydrolyzable by an esterase.

27. The compound of claim 15 being 13,14-dihydro-15-keto-11-dehydroxy-16,16-difluoro-18-methyl-PGE, pharmaceutically acceptable salts thereof or esters hydrolyzable by an esterase.

28. The compound of claim 15 being 13,14-dihydro-15-keto-11-dehydroxy-16,16-difluoro-20,20-dimethyl-PGE, pharmaceutically acceptable salts thereof or esters hydrolyzable by an esterase.

* * * * *